United States Patent
Heinelt et al.

(10) Patent No.: US 8,598,177 B2
(45) Date of Patent: Dec. 3, 2013

(54) IMIDAZOPYRIDAZINES AS PAR1 INHIBITORS, PRODUCTION THEREOF, AND USE AS MEDICAMENTS

(75) Inventors: Uwe Heinelt, Frankfurt am Main (DE); Volkmar Wehner, Frankfurt am Main (DE); Matthias Herrmann, Frankfurt am Main (DE); Karl Schoenafinger, Alzenau (DE); Henning Steinhagen, Sulzbach (DE)

(73) Assignee: Sanofi, Paris (FR)

( * ) Notice: Subject to any disclaimer, the term of this patent is extended or adjusted under 35 U.S.C. 154(b) by 341 days.

(21) Appl. No.: 12/851,198

(22) Filed: Aug. 5, 2010

(65) Prior Publication Data

US 2011/0034456 A1 Feb. 10, 2011

Related U.S. Application Data

(63) Continuation of application No. PCT/EP2009/000409, filed on Jan. 23, 2009.

(30) Foreign Application Priority Data

Feb. 5, 2008 (EP) .................................. 08290113

(51) Int. Cl.
*A61K 31/501* (2006.01)
*A61K 31/50* (2006.01)
*C07D 487/00* (2006.01)

(52) U.S. Cl.
USPC ...................... 514/252.05; 544/236

(58) Field of Classification Search
USPC ...................... 544/236; 514/252.05
See application file for complete search history.

(56) References Cited

FOREIGN PATENT DOCUMENTS

| EP | 1 391 451 A1 | 2/2004 |
| EP | 1 394 152 A1 | 3/2004 |
| EP | 1 813 282 A1 | 8/2007 |

OTHER PUBLICATIONS

Chackalamannil S. et al., "Thrombin Receptor (PAR-1) Antagonists as Novel Antithrombotic Agents", *Expert Opinion on Therapeutic Patents* 16(4):493-505 (Apr. 1, 2006).

International Search Report dated Jul. 29, 2009 received from the European Patent Office from related International Application No. PCT/EP2009/000409.

*Primary Examiner* — Paul V. Ward
(74) *Attorney, Agent, or Firm* — Scully, Scott, Murphy & Presser, P.C.

(57) ABSTRACT

The invention relates to novel compounds of formula I (I)

where $R_1$, $R_2$, $R_3$, $R_4$, $R_5$, $R_6$, $R_7$, $R_8$, $R_9$, $Q_1$, $Q_2$ and $Q_3$ are each as defined below. The compounds of formula I have antithrombotic activity and inhibit especially protease-activated receptor 1 (PAR1). The invention further relates to a process for preparing the compound of formula I and to the use thereof as a medicament.

10 Claims, No Drawings

IMIDAZOPYRIDAZINES AS PAR1 INHIBITORS, PRODUCTION THEREOF, AND USE AS MEDICAMENTS

FIELD OF INVENTION

The invention relates to novel compounds of the formula I

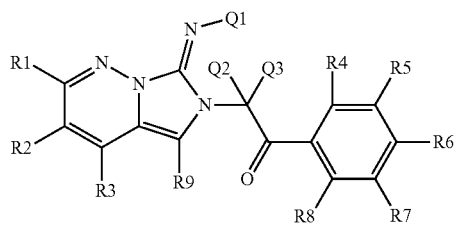

where R1, R2, R3, R4, R5, R6, R7, R8, R9, Q1, Q2 and Q3 are each as defined below. The compounds of the formula I have antithrombotic activity and inhibit especially protease-activated receptor 1 (PAR1). The invention further relates to a process for preparing the compound of the formula I and to the use thereof as a medicament.

BACKGROUND OF THE INVENTION

Protease-activated receptor 1 (PAR1) is a thrombin receptor which belongs to the class of G protein-coupled receptors (GPCR). The gene for PAR1 is located on chromosome 5q13, consists of two exons and covers a region of about 27 kb.

PAR1 is expressed inter alia in endothelial cells, smooth muscle cells, fibroblasts, neurons and human blood platelets. On blood platelets, PAR1 is an important receptor of signal transmission and is involved in initiating the aggregation of blood platelets.

Activation of the PARs takes place by proteolytic elimination of part of the N terminus of the PARs, thus exposing a new N-terminal sequence which then activates the receptor (Pharmacol Rev 54:203-217, 2002).

The coagulation of blood is a process for controlling blood flow which is essential for the survival of mammals. The process of coagulation and the subsequent breakup of the clot after wound healing has taken place starts after damage to a vessel and can be divided into four phases:
1. The phase of vascular constriction: the blood loss into the damaged area is reduced thereby.
2. The next phase is that of platelet adhesion to the exposed collagen in the subendothelium. This primary adhesion to the matrix activates the platelets, which then secrete various activators which lead to enhancement of the activation. These activators additionally stimulate further recruitment of new platelets to the site of vessel damage and promote platelet aggregation. The platelets aggregate at the site of vessel wall damage and form a still loose platelet plug. Activation of platelets further leads to presentation of phosphatidylserine and phosphatidylinositol along the cell membrane surfaces. Exposure of these phospholipids is essential for binding and activating the multienzyme complexes of the coagulation cascade.
3. The initially still loose platelet aggregate is crosslinked by fibrin. If the thrombus comprises platelets and fibrin, it is a white thrombus. If red blood corpuscles are additionally present, it is a red thrombus.
4. After wound healing, the thrombus is broken up by the action of the protein plasmin.

Two alternative pathways lead to the formation of a fibrin clot, the intrinsic and the extrinsic pathway. These pathways are initiated by different mechanisms, but in a later phase they converge to a common pathway of the coagulation cascade. Formation of a red thrombus or a clot on the basis of a vessel wall abnormality without wound is the result of the intrinsic pathway. Fibrin clot formation as response to tissue damage or injury is the result of the extrinsic pathway. Both pathways include a relatively large number of proteins which are known as coagulation factors.

The intrinsic pathway requires coagulation factors VIII, IX, X, XI and XII and prekallikrein, high molecular weight kininogen, calcium ions and phospholipids from platelets. Each of these proteins leads to activation of factor X.

The intrinsic pathway is initiated when prekallikrein, high molecular weight kininogen, factor XI and XII bind to a negatively charged surface. This moment is referred to as the contact phase. Exposure to a vessel wall collagen is the primary stimulus of the contact phase. The result of the contact phase processes is conversion of prekallekrein into kallekrein, which in turn activates factor XII. Factor XIIa hydrolyzes further prekallekrein to kallekrein, so that the result is activation. As the activation of factor XII increases there is activation of factor XI which leads to release of bradykinin, a vasodilator. The initial phase of vasoconstriction is terminated thereby. Bradykinin is produced from the high molecular weight kininogen. In the presence of $Ca^{2+}$ ions, factor XIa activates factor IX. Factor IX is a proenzyme which contains vitamin K-dependent, c-carboxyglutamate (GLA) residues. The serine protease activity becomes evident after $Ca^{2+}$ ions have bound to these GLA residues. Several of the serine proteases in the blood coagulation cascade (factors II, VII, IX and X) contain such vitamin K-dependent GLA residues. Factor IXa cleaves factor X and leads to activation to factor Xa. The precondition for the formation of factor IXa is the formation of a protease complex of $Ca^{2+}$ ions and factors VIIIa, IXa and X on the surface of activated platelets. One of the reactions of activated platelets is the presentation of phosphatidylserine and phosphatidylinositol along the surfaces. Formation of the protease complex is made possible by exposure of these phospholipids. In this process, factor VIII acts as a receptor for factors IXa and X. Factor VIII therefore represents a cofactor in the coagulation cascade. Activation of factor VIII with formation of factor VIIIa, the actual receptor, requires only a minimal amount of thrombin. As the concentration of thrombin increases, factor VIIIa is finally cleaved further, and inactivated, by thrombin. This dual activity of thrombin in relation to factor VIII leads to the protease complex formation being self-limiting and thus the blood coagulation being localized.

PAR1 and PAR4 play a central role in the activation of human blood platelets by thrombin; activation of these receptors leads to morphological changes in blood platelets, release of ADP and aggregation of the blood platelets (Nature 413: 26-27, 2001).

PAR1 inhibitors are described for example in the European patent applications EP1391451 or EP1391452, the US patent applications U.S. Pat. No. 6,063,847 and US 2004/152736, and the international application WO 03/089428.

DESCRIPTION OF THE INVENTION

The compounds of the formula I show a high specific inhibition of protease-activated receptor 1 and are therefore suitable for prophylactic and therapeutic use in humans suffering from disorders associated with thromboses, embolisms, hypercoagulability or fibrotic alterations. Examples of such disorders are thrombosis, deep vein thrombosis, pulmonary embolisms, cerebral infarction, myocardial infarction, high blood pressure, inflammatory disorders, rheumatism, asthma, glomerulonephritis or osteoporosis. The compounds of the formula I can be employed for secondary prevention and are suitable both for acute and for long-term therapy.

The compounds of the formula I can also be employed in combination with active ingredients which act by antithrombotic principles different from PAR1.

1) The invention therefore relates to a compound of the formula I

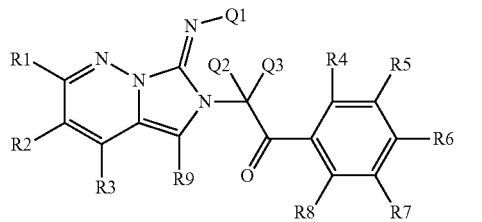

and/or any stereoisomeric or tautomeric forms of the compound of the formula I and/or mixtures of these forms in any ratio, and/or a physiologically compatible salt of the compound of the formula I, where Q1 is a hydrogen atom, —$(C_1$-$C_6)$-alkyl, —$(C_3$-$C_6)$-cycloalkyl, —OH, —O—$(C_1$-$C_6)$-alkyl or —O—$(C_3$-$C_6)$-cycloalkyl, where alkyl and cycloalkyl are each unsubstituted or mono-, di- or trisubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in alkyl or cycloalkyl may be replaced by fluorine, Q2 and Q3 are the same or different and are each independently a hydrogen atom, —$(C_1$-$C_6)$-alkyl or —$(C_3$-$C_6)$-cycloalkyl, where some or all of the hydrogen atoms in alkyl or cycloalkyl may be replaced by fluorine, R1, R2 and R3 are the same or different and are each independently a hydrogen atom, —$(C_1$-$C_6)$-alkyl, —$(C_3$-$C_6)$-cycloalkyl, —O—$(C_1$-$C_8)$-alkyl, —O—$(C_3$-$C_6)$-cycloalkyl, —$(C_0$-$C_4)$-alkylene-C(O)—N(R11)-R12, —$(C_0$-$C_4)$-alkylene-C(O)—O—R11, —$(C_0$-$C_4)$-alkylene-C(O)—R11, —$(C_0$-$C_4)$-alkylene-N(R11)-R12, —$(C_0$-$C_4)$-alkylene-N(R11)-C(O)—R12, halogen, OH, —CN, —$NO_2$, —$SO_2CH_3$, —$SO_2CF_3$, —$SF_5$, —Si[—$(C_1$-$C_4)$-alkyl]$_3$, —$(C_1$-$C_6)$-alkylene-O—$(C_1$-$C_6)$-alkyl, —O—$(C_1$-$C_6)$-alkylene-O—$(C_1$-$C_6)$-alkyl, —O—$(C_0$-$C_4)$-alkylene-$(C_6$-$C_{14})$-aryl where aryl is unsubstituted or mono-, di- or trisubstituted independently by —O—$(C_1$-$C_6)$-alkyl, —$(C_1$-$C_4)$-alkyl, OH, —$(C_3$-$C_6)$-cycloalkyl or —O—$(C_3$-$C_6)$-cycloalkyl, —O—$(C_1$-$C_4)$-alkylene-$(C_3$-$C_6)$-cycloalkyl, —$(C_4$-$C_{15})$-Het, where Het is unsubstituted or mono-, di- or trisubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, or —O—$(C_1$-$C_6)$-alkylene-O—$(C_1$-$C_6)$-alkylene-O—$(C_1$-$C_6)$-alkyl, where alkyl, alkylene and cycloalkyl are each unsubstituted or mono-, di- or trisubstituted independently by —$(C_1$-$C_4)$-alkyl, —$(C_3$-$C_6)$-cycloalkyl, OH, —O—$(C_1$-$C_6)$-alkyl, —$(C_6$-$C_{14})$-aryl where aryl is unsubstituted or mono-, di-, tri-, tetra- or pentasubstituted independently by halogen, —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, —$(C_4$-$C_{15})$-Het where Het is unsubstituted or mono-, di-, tri-, tetra- or pentasubstituted independently by halogen, —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, —O—$(C_3$-$C_6)$-cycloalkyl, or where some or all of the hydrogen atoms in alkyl, alkylene or cycloalkyl may be replaced by fluorine, or R1 and R2 or R2 and R3, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in the 5- to 8-membered ring formed, and in alkyl or cycloalkyl, may be replaced by fluorine, R11 and R12 are each independently a hydrogen atom, —$(C_1$-$C_6)$-alkyl, —$(C_3$-$C_6)$-cycloalkyl, —$(C_0$-$C_4)$-alkylene-$(C_6$-$C_{14})$-aryl, where aryl is unsubstituted or mono-, di- or trisubstituted independently by —O—$(C_1$-$C_6)$-alkyl, —$(C_1$-$C_4)$-alkyl, OH, —$(C_3$-$C_6)$-cycloalkyl or —O—$(C_3$-$C_6)$-cycloalkyl, —$(C_0$-$C_4)$-alkylene-$(C_4$-$C_{15})$-Het, where Het is unsubstituted or mono-, di-, tri-, tetra- or pentasubstituted independently by halogen, $(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, —$SO_2CH_3$ or —$SO_2CF_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, where some or all of the hydrogen atoms in the 5- to 8-membered ring formed, and in alkyl or cycloalkyl, may be replaced by fluorine, R4, R5, R6, R7 and R8 are the same or different and are each independently a hydrogen atom, —$(C_1$-$C_6)$-alkyl, —$(C_3$-$C_6)$-cycloalkyl, OH, —CN, —$NO_2$, —O—$(C_1$-$C_8)$-alkyl, —O—$(C_3$-$C_6)$-cycloalkyl, —$(C_0$-$C_4)$-alkylene-(CO)—N(R21)-R22, —$SO_2CH_3$, —$SO_2CF_3$, —$(C_0$-$C_4)$-alkylene-C(O)—O—R21, halogen, —$SF_5$, —$(C_0$-$C_4)$-alkylene-C(O)—R21, —$(C_0$-$C_4)$-alkylene-N(R21)-R22, —$(C_0$-$C_4)$-alkylene-N(R21)-C(O)—R22, —$(C_1$-$C_6)$-alkylene-β-$(C_1$-$C_6)$-alkyl, —$(C_0$-$C_6)$-alkylene-O—$(C_1$-$C_6)$-alkylene-O—$(C_1$-$C_6)$-alkyl, —Si[—$(C_1$-$C_4)$-alkyl]$_3$, —$(C_0$-$C_6)$-alkylene-O—$(C_1$-$C_4)$-alkylene-$(C_3$-$C_6)$-cycloalkyl, —$(C_0$-$C_6)$-alkylene-O—$(C_0$-$C_6)$-alkylene-$(C_6$-$C_{14})$-aryl or —$(C_4$-$C_{15})$-Het, where alkyl, alkylene and cycloalkyl are each unsubstituted or mono-, di- or trisubstituted independently by —$(C_1$-$C_4)$-alkyl, —$(C_3$-$C_6)$-cycloalkyl, OH, —O—$(C_1$-$C_6)$-alkyl, —$(C_6$-$C_{14})$-aryl where aryl is unsubstituted or mono-, di-, tri-, tetra- or pentasubstituted independently by halogen, —$(C_1$-$C_4)$-alkyl, —$(C_3$-$C_6)$-cycloalkyl, OH, —O—$(C_1$-$C_6)$-alkyl or —O—$(C_3$-$C_6)$-cycloalkyl, —$(C_4$-$C_{15})$-Het where Het is unsubstituted or mono-, di-, tri-, tetra- or pentasubstituted independently by halogen, —$(C_1$-$C_4)$-alkyl, —$(C_3$-$C_6)$-cycloalkyl, OH, —O—($C_1$-$C_6$)-alkyl or —O—($C_3$-$C_6$)-cycloalkyl, or —O—($C_3$-$C_6$)-cycloalkyl,
where some or all of the hydrogen atoms in alkyl, alkylene or cycloalkyl may be replaced by fluorine, or R4 and R5, R5 and R6, R6 and R7 or R7 and R8, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine, R9 is a hydrogen atom, —($C_1$-$C_6$)-alkyl, —($C_3$-$C_6$)-cycloalkyl, —($C_0$-$C_4$)-alkylene-($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —($C_0$-$C_4$)-alkylene-($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, and where all or some of the hydrogen atoms in alkyl, alkylene or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl,
—($C_0$-$C_4$)-alkylene-($C_4$-$C_{15}$)-Het, where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl,
—$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine.

2) Preference is given to a compound of the formula I wherein
Q1, Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine,
R1, R2 and R3 are the same or different and are each independently a hydrogen atom, —($C_1$-$C_6$)-alkyl, —($C_3$-$C_6$)-cycloalkyl, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$,
—$SO_2CF_3$, —$SF_5$, —Si[—($C_1$-$C_4$)-alkyl]$_3$, —($C_1$-$C_6$)-alkylene-O—($C_1$-$C_6$)-alkyl, —O—($C_0$-$C_4$)-alkylene-O—($C_1$-$C_6$)-alkyl, —O—($C_0$-$C_4$)-alkylene-($C_6$-$C_{14}$)-aryl where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl, —O—($C_1$-$C_4$)-alkylene-($C_3$-$C_6$)-cycloalkyl, —($C_4$-$C_{15}$)-Het,
where Het is unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_1$-$C_6$)-alkylene-O—($C_1$-$C_6$)-alkylene-O—($C_1$-$C_6$)-alkyl,
where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or
where some or all of the hydrogen atoms in alkyl, alkylene or cycloalkyl may be replaced by fluorine,
with the proviso that at least one R1, R2 or R3 is not a hydrogen atom or R1 and R2 or R2 and R3, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl,
—($C_0$-$C_4$)-alkylene-($C_4$-$C_{15}$)-Het, where Het is unsubstituted or mono-, di-, tri-, tetra- or pentasubstituted independently by halogen, ($C_1$-$C_4$)-alkyl, —($C_3$-$C_6$)-cycloalkyl, OH, —O—($C_1$-$C_6$)-alkyl or —O—($C_3$-$C_6$)-cycloalkyl,
—$SO_2CH_3$ or —$SO_2CF_3$,
where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—(CO)" group to form cyclic amines, imides or lactams which contain up to 2 further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, R4, R5, R6, R7 and R8 are the same or different and are each independently a hydrogen atom, —($C_1$-$C_6$)-alkyl, —($C_3$-$C_6$)-cycloalkyl, OH, —CN, —$NO_2$, —O—($C_1$-$C_8$)-alkyl, —O—($C_3$-$C_6$)-cycloalkyl, —($C_0$-$C_4$)-alkylene-(CO)—N(R21)-R22, —$SO_2CH_3$, —$SO_2CF_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-β-($C_1$-$C_6$)-alkyl, —($C_0$-$C_6$)-alkylene-O—($C_1$-$C_6$)-alkylene-O—

$(C_1-C_6)$-alkyl, —Si[—$(C_1-C_4)$-alkyl]$_3$, —$(C_0-C_6)$-alkylene-O—$(C_1-C_4)$-alkylene-$(C_3-C_6)$-cycloalkyl, —$(C_0-C_6)$-alkylene-O—$(C_0-C_6)$-alkylene-$(C_6-C_{14})$-aryl or —$(C_4-C_{15})$-Het, where alkyl, alkylene and cycloalkyl are each unsubstituted or mono-, di- or trisubstituted independently by —$(C_1-C_4)$-alkyl, —$(C_3-C_6)$-cycloalkyl, OH, —O—$(C_1-C_6)$-alkyl, —$(C_6-C_{14})$-aryl where aryl is unsubstituted or mono-, di-, tri-, tetra- or pentasubstituted independently by halogen, —$(C_1-C_4)$-alkyl, —$(C_3-C_6)$-cycloalkyl, OH, —O—$(C_1-C_6)$-alkyl or —O—$(C_3-C_6)$-cycloalkyl, —$(C_4-C_{15})$-Het where Het is unsubstituted or mono-, di-, tri-, tetra- or pentasubstituted independently by halogen, —$(C_1-C_4)$-alkyl, —$(C_3-C_6)$-cycloalkyl, OH, —O—$(C_1-C_6)$-alkyl or —O—$(C_3-C_6)$-cycloalkyl, or —O—$(C_3-C_6)$-cycloalkyl, or where some or all of the hydrogen atoms in alkyl, alkylene or cycloalkyl may be replaced by fluorine, with the proviso that at least one R4, R5, R6, R7 or R8 is not a hydrogen atom, or R4 and R5, R5 and R6, R6 and R7 or R7 and R8, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, where some or all of the hydrogen atoms in alkyl or cycloalkyl may be replaced by fluorine, R9 is a hydrogen atom, —$(C_1-C_6)$-alkyl, —$(C_3-C_6)$-cycloalkyl, —$(C_0-C_4)$-alkylene-$(C_6-C_{14})$-aryl, where aryl is unsubstituted or mono-, di- or trisubstituted independently by —O—$(C_1-C_6)$-alkyl, —$(C_1-C_4)$-alkyl, OH, —$(C_3-C_6)$-cycloalkyl or —O—$(C_3-C_6)$-cycloalkyl, —$(C_0-C_4)$-alkylene-$(C_4-C_{15})$-Het where Het is unsubstituted or mono-, di-, tri-, tetra- or pentasubstituted independently by halogen, —$(C_1-C_4)$-alkyl, —$(C_3-C_6)$-cycloalkyl, OH, —O—$(C_1-C_6)$-alkyl or —O—$(C_3-C_6)$-cycloalkyl, and where all or some of the hydrogen atoms in alkyl, alkylene or cycloalkyl may be replaced by fluorine, R21 and R22 are each independently a hydrogen atom, —$(C_1-C_6)$-alkyl, —$(C_3-C_6)$-cycloalkyl, —$(C_0-C_4)$-alkylene-$(C_6-C_{14})$-aryl, where aryl is unsubstituted or mono-, di- or trisubstituted independently by —O—$(C_1-C_6)$-alkyl, —$(C_1-C_4)$-alkyl, OH, —$(C_3-C_6)$-cycloalkyl or —O—$(C_3-C_6)$-cycloalkyl, —$(C_0-C_4)$-alkylene-$(C_4-C_{15})$-Het, where Het is unsubstituted or mono-, di-, tri-, tetra- or pentasubstituted independently by halogen, $(C_1-C_4)$-alkyl, —$(C_3-C_6)$-cycloalkyl, OH, —O—$(C_1-C_6)$-alkyl or —O—$(C_3-C_6)$-cycloalkyl, —SO$_2$CH$_3$ or —SO$_2$CF$_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to 2 further heteroatoms from the group of N, O and S, where the ring is unsubstituted or mono- or disubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, where some or all of the hydrogen atoms in alkyl or cycloalkyl may be replaced by fluorine.

3) Particular preference is given to a compound of the formula I, wherein

Q1, Q2 and Q3 are the same or different and are each independently a hydrogen atom, —$(C_1-C_6)$-alkyl or —$(C_3-C_6)$-cycloalkyl, where some or all of the hydrogen atoms in alkyl or cycloalkyl may be replaced by fluorine, R1, R2 and R3 are the same or different and are each independently a hydrogen atom, —$(C_1-C_6)$-alkyl, —$(C_3-C_6)$-cycloalkyl, —O—$(C_1-C_8)$-alkyl, —O—$(C_3-C_6)$-cycloalkyl, —$(C_0-C_4)$-alkylene-C(O)—N(R11)-R12, —$(C_0-C_4)$-alkylene-C(O)—O—R11, —$(C_0-C_4)$-alkylene-C(O)—R11, —$(C_0-C_4)$-alkylene-N(R11)-R12, —$(C_0-C_4)$-alkylene-N(R11)-C(O)—R12, halogen, OH, —CN, —NO$_2$, —SO$_2$CH$_3$, —Si[—$(C_1-C_4)$-alkyl]$_3$, —$(C_1-C_6)$-alkylene-O—$(C_1-C_6)$-alkyl, —O—$(C_1-C_6)$-alkylene-O—$(C_1-C_6)$-alkyl, —O—$(C_0-C_4)$-alkylene-$(C_6-C_{14})$-aryl, —O—$(C_1-C_4)$-alkylene-$(C_3-C_6)$-cycloalkyl, —$(C_4-C_{15})$-Het or —O—$(C_1-C_6)$-alkylene-O —$(C_1-C_6)$-alkylene-O—$(C_1-C_6)$-alkyl, where alkyl, alkylene and cycloalkyl are each unsubstituted or mono-, di- or trisubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, or where some or all of the hydrogen atoms in alkyl, alkylene or cycloalkyl may be replaced by fluorine, with the proviso that at least one R1, R2 or R3 is not a hydrogen atom or R1 and R2 or R2 and R3, together with the ring atoms to which they are each bonded, form a ring selected from the group of 2,3,5,6,7,8-hexahydro-1,2,3a,4,5,8-hexaaza-cyclopenta[b]naphthalene; 2,6,7,8-tetrahydro-3H-5-oxa-1,2,3a,4,8-pentaaza-cyclopenta[b]naphthalene; 2,3,6,7-tetrahydro-5,8-dioxa-1,2,3a,4-tetraaza-cyclopenta[b]naphthalene; 2,3,6,7-tetrahydro-5H-8-oxa-1,2,3a,4,5-pentaaza-cyclopenta[b]naphthalene; 2,6,7,8-tetrahydro-3H-5-thia-1,2,3a,4,8-pentaaza-cyclopenta[b]naphthalene; 2,3,6,7,8,9-hexahydro-1,2,3a,4,6,9-hexaaza-cyclopenta[a]-naphthalene; 2,3-dihydro-5,7-dioxa-1,2,3a,4-tetraaza-s-indacene; 2,6,7,8-tetrahydro-3H-cyclopenta[e][1,2,4]triazolo[4,3-b]pyridazine; 2,7,8,9-tetrahydro-3H-cyclopenta[d][1,2,4]triazolo[4,3-b]pyridazine and 2,3,6a,9a-tetrahydro-[1,3]dioxolo[4,5-d][1,2,4]triazolo[4,3-b]pyridazine, where the ring is unsubstituted or mono- or disubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl, where some or all of the hydrogen atoms in alkyl or cycloalkyl may be replaced by fluorine, R11 and R12 are each independently a hydrogen atom, —$(C_1-C_6)$-alkyl, —$(C_3-C_6)$-cycloalkyl, —$(C_0-C_4)$-alkylene-$(C_6-C_{14})$-aryl, —$(C_0-C_4)$-alkylene-$(C_4-C_{15})$-Het, —SO$_2$CH$_3$ or —SO$_2$CF$_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —$(C_1-C_4)$-alkyl, —$(C_3-C_6)$-cycloalkyl, OH, —O—$(C_1-C_6)$-alkyl or —O—$(C_3-C_6)$-cycloalkyl where some or all of the hydrogen atoms in alkyl or cycloalkyl may be replaced by fluorine, R4, R5, R6, R7 and R8 are the same or different and are each independently a hydrogen atom, —$(C_1-C_6)$-alkyl, —$(C_3-$ $C_6$)-cycloalkyl, OH, —CN, —$NO_2$, —O—($C_1$-$C_8$)-alkyl, —O—($C_3$-$C_6$)-cycloalkyl, —($C_0$-$C_4$)-alkylene-(CO)—N(R21)-R22, —$SO_2CH_3$, —$SO_2CF_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —($C_0$-$C_6$)-alkylene-O—($C_1$-$C_6$)-alkylene-O—($C_1$-$C_6$)-alkyl, —Si[—($C_1$-$C_4$)-alkyl]$_3$, —($C_0$-$C_6$)-alkylene-O—($C_1$-$C_4$)-alkylene-($C_3$-$C_6$)-cycloalkyl, —($C_0$-$C_6$)-alkylene-O—($C_0$-$C_6$)-alkylene-($C_6$-$C_{14}$)-aryl or —($C_4$-$C_{15}$)-Het,
- where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, —($C_4$-$C_{15}$)-Het where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or —O—($C_3$-$C_6$)-cycloalkyl, or
- where some or all of the hydrogen atoms in alkyl, alkylene or cycloalkyl may be replaced by fluorine, with the proviso that at least one R4, R5, R6, R7 or R8 is not a hydrogen atom, or R4 and R5, R5 and R6, R6 and R7 or R7 and R8, together with the ring atoms to which they are each bonded, form a 5- to 8-membered ring selected from the group of 2,3-dihydrobenzo[1,4]dioxin; 3,4-dihydro-2H-benzo[1,4]oxazine; 1,2,3,4-tetrahydro-quinoxaline; benzo[1,3]dioxole; 3,4-dihydro-2H-benzo[1,4]thiazine and 2,3,4,5-tetrahydro-1H-benzo[b][1,4]diazepine,
- where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, R9 is a hydrogen atom, —($C_1$-$C_6$)-alkyl or —($C_3$-$C_6$)-cycloalkyl, where some or all of the hydrogen atoms in alkyl or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring selected from the group of azetidinyl, pyrrolidinyl, piperidinyl, piperazinyl, azepinyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in the 5- to 8-membered ring formed, and in alkyl or cycloalkyl, may be replaced by fluorine.

4) The invention further relates to a compound of the formula I, wherein

Q1, Q2 and Q3 are the same and are each a hydrogen atom,

R1, R2 and R3 are the same or different and are each independently a hydrogen atom, —($C_1$-$C_4$)-alkyl, —O—$CH_2$—$CF_3$ or —O—($C_1$-$C_6$)-alkyl, with the proviso that at least one R1, R2 or R3 is not a hydrogen atom, R4, R5, R6, R7 and R8 are the same or different and are each independently a hydrogen atom, —($C_1$-$C_6$)-alkyl, —O—($C_1$-$C_4$)-alkyl, —$SF_5$ or —N(R21)-R22, with the proviso that at least one R4, R5, R6, R7 or R8 is not a hydrogen atom, and R9 is a hydrogen atom, R21 and R22 are each independently a hydrogen atom or —($C_1$-$C_4$)-alkyl, or R21 and R22 in the "N(R21)-R22" fragment represent a 5- to 8-membered ring, selected from the group of azetidinyl, pyrrolidinyl, piperidinyl, piperazinyl, azepinyl, imidazolyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl.

5) Exceptionally preferred are compounds of the formula I including the following compounds:
1-(3-tert-butyl-4-methoxy-5-morpholin-4-ylphenyl)-2-(7-imino-2,3-dimethoxyimidazo-[1,5-b]pyridazin-6-yl)ethanone as trifluoroacetic acid salt,
1-(3-tert-butyl-4-methoxy-5-morpholin-4-ylphenyl)-2-(2,3-diethoxy-7-iminoimidazo[1,5-b]-pyridazin-6-yl)ethanone as trifluoroacetic acid salt,
N-{3-[2-(2,3-diethoxy-7-iminoimidazo[1,5-b]pyridazin-6-yl)acetyl]-5-pentafluoro-sulfanylphenyl}acetamide as trifluoroacetic acid salt,
1-(3-tert-butyl-4-methoxy-5-morpholin-4-ylphenyl)-2-[7-imino-2-methoxy-3-(2,2,2-trifluoro-ethoxy)imidazo[1,5-b]pyradizin-6-yl]ethanone, 2-(2,3-diethoxy-7-iminoimidazol[1,5-b]-pyridazin-6-yl)-1-(5-methylamino-3-pentafluorosulfanylphenyl)ethanone or
2-(2,3-diethoxy-7-iminoimidazo[1,5-b]pyridazin-6-yl)-1-[3-methylamino-5-(pentafluoro-sulfanyl)phenyl]ethanone.

The expression "($C_1$-$C_4$)-alkyl" or "($C_1$-$C_6$)-alkyl" is understood to mean hydrocarbon radicals whose carbon chain is straight-chain or branched and contains from 1 to 4 carbon atoms or from 1 to 6 carbon atoms, for example methyl, ethyl, propyl, isopropyl, butyl, isobutyl, sec-butyl, tert-butyl, pentyl, isopentyl, neopentyl, 1-ethylpropyl, hexyl, 2,3-dimethylbutyl or neohexyl.

The expression "—($C_0$-$C_4$)-alkylene" or "—($C_1$-$C_6$)-alkylene" is understood to mean hydrocarbon radicals whose carbon chain is straight-chain or branched and contains 1 to 4 or 1-6 carbon atoms, for example methylene, ethylene, 1-methylmethylene, propylene, 1-methylethylene, butylene, 1-propylmethylene, 1-ethyl-1-methylmethylene, 1,2-dimethylethylene, 1,1-dimethylmethylene, 1-ethylethylene, 1-methylpropylene, 2-methylpropylene, pentylene, 1-methylbutylene, hexylene, 1-methylpentylene. "–$C_0$-alkylene" is a covalent bond.

The expression "—O—($C_1$-$C_6$)-alkyl" or "—O—($C_1$-$C_8$)-alkyl" is understood to mean alkoxy radicals whose carbon chain is straight-chain or branched and contains 1 to 6 or from 1 to 8 carbon atoms, for example methoxy, ethoxy, propoxy, isopropoxy, butoxy, isobutoxy, tert-butoxy, 1-pentoxy, 2-pentoxy, 3-pentoxy, 1-hexoxy, 2-hexoxy, 3-hexoxy, 1-heptoxy, 2-heptoxy, 3-heptoxy, 4-heptoxy, 2,4-dimethylpentan-3-oxy, 1-octoxy, 2-octoxy, 3-octoxy, 2,2,4-trimethylpentan-3-oxy, 2,3,4-trimethylpentan-3-oxy or 4-octoxy. The expression "($C_3$-$C_6$)-cycloalkyl" is understood to mean radicals such as compounds which derive from 3- to 6-membered monocycles such as cyclopropane, cyclobutane, cyclopentane or cyclohexane.

The expression "—O—(C₃-C₆)-cycloalkyl" is understood to mean cycloalkoxy radicals such as compounds which derive from 3- to 6-membered monocycles such as cyclopropoxy, cyclobutoxy, cyclopentoxy or cyclohexoxy.

The expression "—(C₆-C₁₄)-aryl" is understood to mean aromatic carbon radicals having from 6 to 14 carbon atoms in the ring. —(C₆-C₁₄)-Aryl radicals are, for example, phenyl, naphthyl, for example 1-naphthyl, 2-naphthyl, anthryl or fluorenyl. Naphthyl radicals and especially phenyl are preferred aryl radicals.

The expression "Het" is understood to mean ring systems having from 4 to 15 carbon atoms which are present in one, two or three ring systems joined to one another and which, according to ring size, may contain one, two, three or four identical or different heteroatoms from the group of oxygen, nitrogen and sulfur. Examples of these ring systems are acridinyl, azepinyl, azetidinyl, benzimidazolyl, benzofuranyl, benzothiofuranyl, benzothiophenyl, benzoxazolyl, benzothiazolyl, benzotriazolyl, benzisoxazolyl, benzisothiazolyl, carbazolyl, 4aH-carbazolyl, carbolinyl, quinazolinyl, quinolinyl, 4H-quinolizinyl, quinoxalinyl, quinuclidinyl, chromanyl, chromenyl, cinnolinyl, decahydroquinolinyl, dibenzofuranyl, dibenzothiophenyl, dihydrofuran[2,3-b]-tetrahydrofuranyl, dihydrofuranyl, dioxolyl, dioxanyl, 2H,6H-1,5,2-dithiazinyl, furanyl, furazanyl, imidazolidinyl, imidazolinyl, imidazolyl, 1H-indazolyl, indolinyl, indolizinyl, indolyl, 3H-indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxothiolanyl, phenanthridinyl, phenanthrolinyl, phenazinyl, phenothiazinyl, phenoxathiinyl, phenoxazinyl, phthalazinyl, piperazinyl, piperidinyl, pteridinyl, purynyl, pyranyl, pyrazinyl, pyroazolidinyl, pyrazolinyl, pyrazolyl, pyridazinyl, pryidooxazolyl, pyridoimidazolyl, pyridothiazolyl, pyridothiophenyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrahydropyridinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolidinyl, thiazolinyl, thiazolyl, thienyl, thienoimidazolyl, thienooxazolyl, thienopyrrolyl, thienopyridyl, thienothiazolyl, thienothiophenyl, thiomorpholinyl, triazinyl, 1,2,3-triazolyl, 1,2,4-triazolyl, 1,2,5-triazolyl, 1,3,4-triazolyl or xanthenyl radicals.

The expression "R1 and R2 or R2 and R3, together with the ring atoms to which they are each bonded, form a 5- to 8-membered ring, where the ring consists only of carbon atoms or 1, 2 or 3 of these atoms are replaced by nitrogen, oxygen or sulfur atoms" is understood to mean, for example, ring systems such as 2,3,5,6,7,8-hexahydro-1,2,3a,4,5,8-hexaaza-cyclopenta[b]-naphthalene; 2,6,7,8-tetrahydro-3H-5-oxa-1,2,3a,4,8-pentaaza-cyclopenta[b]naphthalene; 2,3,6,7-tetrahydro-5,8-dioxa-1,2,3a,4-tetraaza-cyclopenta[b]naphthalene; 2,3,6,7-tetrahydro-5H-8-oxa-1,2,3a,4,5-pentaaza-cyclopenta[b]naphthalene; 2,6,7,8-tetrahydro-3H-5-thia-1,2,3a,4,8-pentaaza-cyclopenta[b]naphthalene; 2,3,6,7,8,9-hexahydro-1,2,3a,4,6,9-hexaaza-cyclopenta[a]naphthalene; 2,3-dihydro-5,7-dioxa-1,2,3a,4-tetraaza-s-indacene; 2,6,7,8-tetrahydro-3H-cyclopenta[e][1,2,4]triazolo[4,3-b]pyridazine; 2,7,8,9-tetrahydro-3H-cyclopenta[d][1,2,4]triazolo[4,3-b]pyridazine or 2,3,6a,9a-tetrahydro-[1,3]dioxolo[4,5-d][1,2,4]-triazolo[4,3-b]pyridazine.

The expression "R4 and R5, R5 and R6, R6 or R7 or R7 and R8, together with the ring atoms to which they are each bonded, form a 5- to 8-membered ring, where the ring consists only of carbon atoms or 1, 2 or 3 of these atoms are replaced by nitrogen, oxygen or sulfur atoms" is understood to mean, for example, ring systems such as 2,3-dihydrobenzo[1,4]dioxin; 3,4-dihydro-2H-benzo[1,4]oxazine; 1,2,3,4-tetrahydroquinoxaline; benzo[1,3]dioxole; 3,4-dihydro-2H-benzo[1,4]thiazine or 2,3,4,5-tetrahydro-1H-benzo[b][1,4]diazepine. The expressions "R11 and R12 in the "N(R11)-R12" and "N(R11)-C(O)—R12" fragments represent a 5- to 8-membered ring which is formed together with the nitrogen atom "N" or the "N—(CO)" group to form cyclic amines, imides or lactams which contain up to 2 further heteroatoms from the group of N, O and S" or "R11 and R12 in the "N(R21)-R22" and "N(R21)-C(O)—R22" fragments is a 5- to 8-membered ring which is formed together with the nitrogen atom "N" or the "N—(CO)" group to form cyclic amines, imides or lactams which contain up to 2 further heteroatoms from the group of N, O and S" is understood to mean, for example, ring systems such as cyclic amines such as azetidinyl, pyrrolidinyl, piperidinyl, piperazinyl, azepinyl, morpholinyl or thiomorpholinyl, and in the case of the imides radicals such as pyrrolidine-2,5-dionyl, piperidine-2,6-dionyl, piperazine-2,6-dionyl, morpholine-3,5-dionyl, and in the case of the lactams radicals such as pyrrolidin-2-onyl, piperidin-2-onyl, piperazin-2-onyl, morpholin-3-onyl.

The rearranged expression "alkyl, alkylene or cycloalkyl some or all of the hydrogen atoms are replaced by fluorine" is understood to mean a partially fluorinated or perfluorinated alkyl, alkylene or cycloalkyl which derives, for example, for alkyl from the following radicals: —CF₃, —CHF₂, —CH₂F, —CHF—CF₃, —CHF—CHF₂, —CHF—CH₂F, —CH₂—CF₃, —CH₂—CHF₂, —CH₂—CH₂F, —CF₂—CF₃, —CF₂—CHF₂, —CF₂—CH₂F, —CH₂—CHF—CF₃, —CH₂—CHF—CHF₂, —CH₂—CHF—CH₂F, —CH₂—CH₂—CF₃, —CH₂—CH₂—CHF₂, —CH₂—CH₂—CH₂F, —CH₂—CF₂—CF₃, —CH₂—CF₂—CHF₂, —CH₂—CF₂—CH₂F, —CHF—CHF—CF₃, —CHF—CHF—CHF₂, —CHF—CHF—CH₂F, —CHF—CH₂—CF₃, —CHF—CH₂—CHF₂, —CHF—CH₂—CH₂F, —CHF—CF₂—CF₃, —CHF—CF₂—CHF₂, —CHF—CF₂—CH₂F, —CF₂—CHF—CF₃, —CF₂—CHF—CHF₂, —CF₂—CHF—CH₂F, —CF₂—CH₂—CF₃, —CF₂—CH₂—CHF₂, —CF₂—CH₂—CH₂F, —CF₂—CF₂—CF₃, —CF₂—CF₂—CHF₂, —CF₂—CF₂—CH₂F, —CH(CF₃)₂, —CH(CHF₂)₂, —CH(CFH₂)₂, —CH(CFH₂)(CHF₂), —CH(CFH₂)(CF₃), —CH(CFH₂)(CH₃), —CH(CHF₂)(CH₃), —CH(CF₃)(CH₃), —CF(CF₃)₂, —CF(CHF₂)₂, —CF(CFH₂)₂, —CF(CFH₂)(CHF₂), —CF(CFH₂)(CF₃), —CF(CFH₂)(CH₃), —CF(CHF₂)(CH₃), —CF(CF₃)(CH₃), and also the further possible combinations for butyl, pentyl and hexyl, which, like propyl, may also be branched, for alkylene, for example, from the following radicals: —CF₂—, —CHF—, —CHF—CF₂—, —CHF—CHF—, —CHF—CH₂—, —CF₂—CF₂—, —CF₂—CH₂F, and also the further possible combinations for propylene, butylene, pentylene and hexylene, which may also be branched, and for cycloalkyl, for example, from the radicals -continued

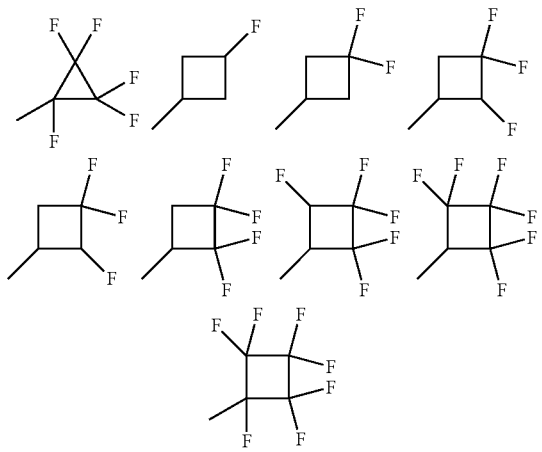

and also the analogous larger cyclopentyl and cyclohexyl rings.

The expression "hal" is understood to mean fluorine, chlorine, bromine or iodine, preference being given to fluorine, chlorine or bromine, especially to fluorine or chlorine.

The expressions described above can also be combined as desired, as done, for example, in "—$(C_0$-$C_6)$-alkylene-O—$(C_0$-$C_6)$-alkylene-$(C_6$-$C_{14})$-aryl".

Functional groups of the intermediates used, for example amino or carboxyl groups in the compound of the formula I, may be masked by suitable protecting groups. Suitable protecting groups for amino functions are, for example, the t-butoxycarbonyl, the benzyloxycarbonyl or the phthaloyl group, and also the trityl or tosyl protecting group. Suitable protecting groups for the carboxyl function are, for example, alkyl, aryl or arylalkyl esters. Protecting groups can be introduced and removed by techniques which are well known or are described here (see Greene, T. W., Wuts, P. G. M., Protective Groups in Organic Synthesis (1999), 3rd Ed., Wiley-Interscience, or Kocienski, P. J., Protecting Groups (2004), 3rd Ed., Thieme. The expression "protecting group" may also include corresponding polymer-bound protecting groups. The inventive compounds can be prepared by well-known processes or by processes described here.

The invention further relates to a process for preparing the compound of the formula I and/or a stereoisomeric form of the compound of the formula I and/or a physiologically compatible salt of the compound of the formula I, which comprises a) reacting a compound of the formula II

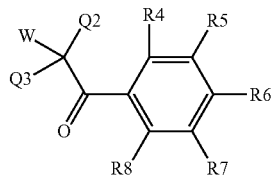

where R4, R5, R6, R7, R8, Q2 and Q3 are each as defined in formula I and W is chloride, bromide, mesylate or tosylate with a compound of the formula III

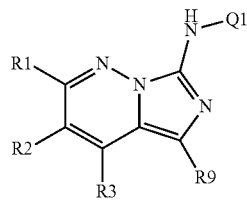

where R1, R2, R3, R9 and Q1 are each as defined in formula I, with or without addition of base, in a solvent to give a compound of the formula I, or b) reacting a compound of the formula VII,

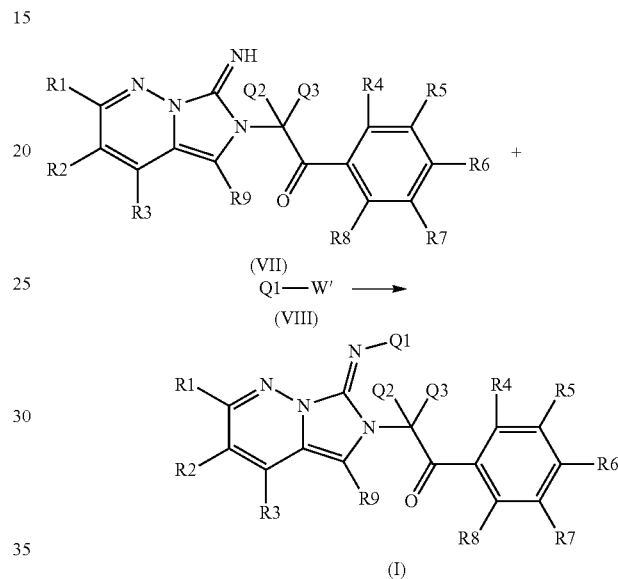

where R1, R2, R3, R4, R5, R6, R7, R8, R9, Q2 and Q3 are each as defined in formula I with a compound Q1-W' where W' is chloride, bromide, tosylate, mesylate, methylsulfate or a similarly good leaving group, with or without addition of base, to give a compound of the formula I, or c) reacting a compound of the formula XXVI

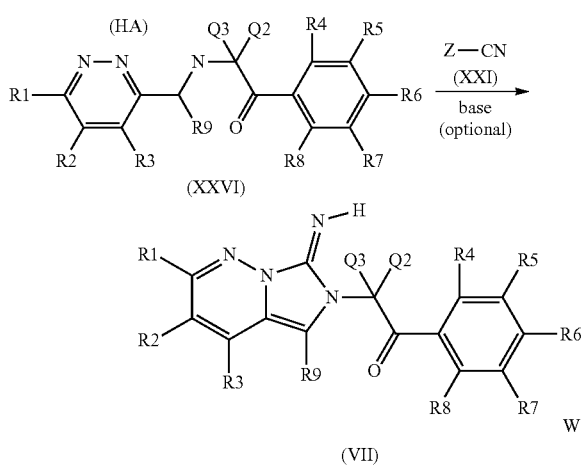

where R1, R2, R3, R4, R5, R6, R7, R8, R9, Q2 and Q3 are each as defined in formula I with a compound Z—CN where Z is a good leaving group such as tosylate, chloride or bromide, with or without addition of base, to give a compound of the formula VII, or d) reacting a compound of the formula XXVII

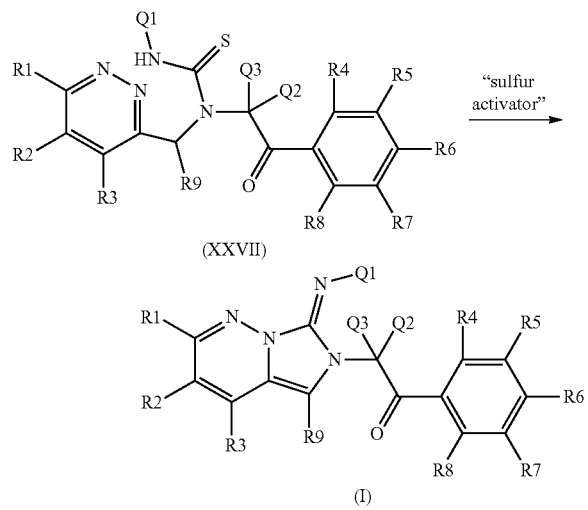

(XXVII)

(I)

where R1, R2, R3, R4, R5, R6, R7, R8, R9, Q1, Q2 and Q3 are each as defined in formula I with a sulfur activator to give a compound of the formula I, or e) either isolating the compound of the formula I prepared by methods a) to d) in free form or releasing it from physiologically incompatible salts or, in the case of the presence of acidic or basic groups, converting it to physiologically compatible salts, or f) separating a compound of the formula I prepared by methods a) to d), or a suitable precursor of the formula I which, owing to its chemical structure, occurs in enantiomeric or diastereomeric forms, into the pure enantiomers or diastereomers by salt formation with enantiomerically pure acids or bases, chromatography on chiral stationary phases or derivatization by means of chiral enantiomerically pure compounds such as amino acids, separation of the diastereomers thus obtained, and elimination of the chiral auxiliary groups.

The invention further relates to a process for preparing the compound of the formula I according to scheme 1.

Scheme 1:

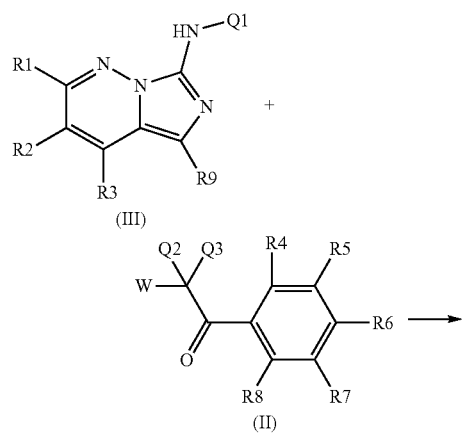

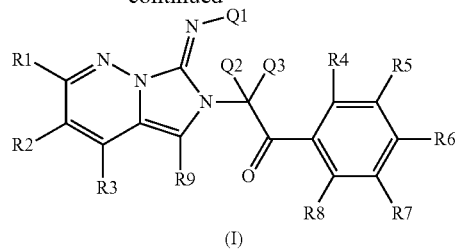

(I)

The reactants II and III, II optionally being present in the form of a salt, are converted at room temperature or a slightly elevated temperature from 40° C. to 60° C., advantageously, when II is in the form of a salt, in the presence of a base, preferably Hünig's base, in a solvent, preferably dimethylformamide (DMF), THF or dioxane, to give the compound of the formula I. The R1, R2, R3, R4, R5, R6, R7, R8, R9, Q1, Q2 and Q3 radicals are each as defined in formula I, W represents a good leaving group such as chloride, bromide, mesylate or tosylate, preferably bromide or mesylate.

Compounds of the formula II can be obtained commercially or by literature methods, for example proceeding from the corresponding acetophenones X or X' (see, for example: Phosphorus and Sulfur and the Related Elements (1985), 25(3), 357 or Tetrahedron Letters (1984), 25(34), 3715). The well-known compounds of the X type, which are commercially available in numerous structural variations, can, for example, be functionalized on the acetyl group with, among other reagents, elemental chlorine or bromine, tribromide derivatives such as phenyltrimethylammonium tribromide, 1,3-dichlorodimethylhydantoin, N-chloro- or N-bromosuccinimide. Compounds of the X' type can be converted, for example, using mesyl or tosyl chloride to the compounds of the II type.

Scheme 2:

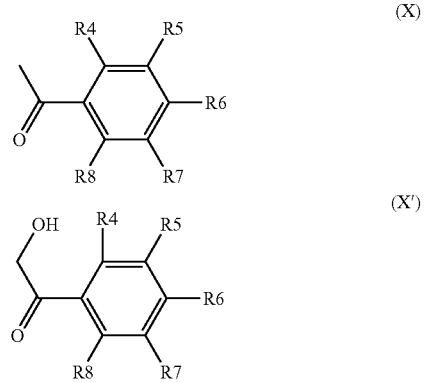

For particular R4 to R8 radicals, it may be more favorable first to convert the ketones of the X type to the ketals of the XI or XI' type, which can then be functionalized, preferably brominated, very selectively on the methyl group to give the compounds of the XII type, and, after deketalization with suitable acids, likewise lead to compounds of the II type. The substituents in schemes 2 and 3 are each as defined above, T is a —($C_1$-$C_4$)-alkyl group, while T' is ethylene, propylene or butylene, W' is a reactive compound such as phenyltrimethylammonium tribromide, N-bromosuccinimide or N-chlorosuccinimide.

Scheme 3:

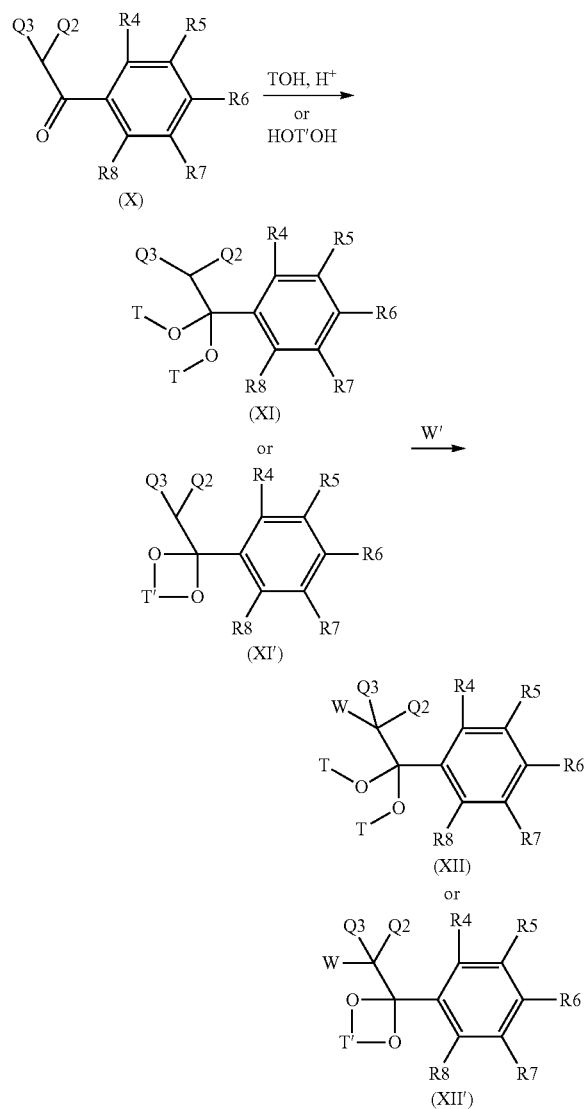

To synthesize compounds of the formula III' type (formula III type where Q1=H), compounds of the formula XX—optionally in the form of their salts (HA)—are preferably cyclized in the presence of a base with a cyano source of the XXI type to give the desired imidazopyridines. Useful acids HA are preferably HBr, HCl, trifluoroacetic acid (TFA) and sulfuric acid. Z is a good leaving group, preferably tosylate, chloride or bromide.

Scheme 4:

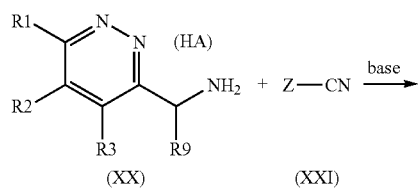

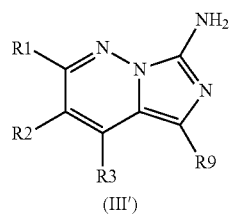

Alternatively, it is possible to obtain compounds of the formula III type by reactions with isothiocyanates of the formula XXII type, forming thioureas of the XXIII type as intermediates. These can then be converted with "sulfur activators", such as methyl iodide, mercury oxide or ethyl bromoacetate, to the desired compounds of the formula III type.

Scheme 5:

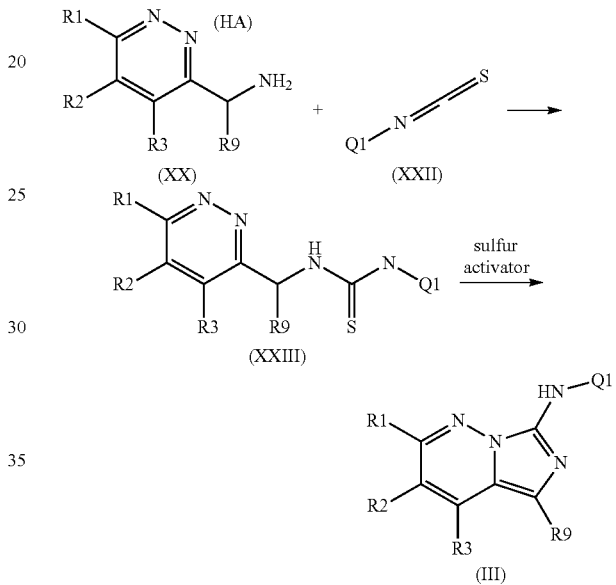

Compounds of the formula XX type are commercially available or can be obtained according to scheme 6.

Scheme 6:

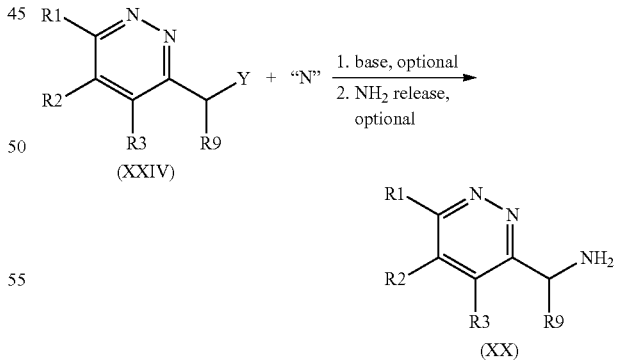

This converts pyridazines of the XXIV type in the presence of a nitrogen nucleophile "N", optionally with a further reaction to release the —NH$_2$ group, to the pyridazinylmethylamines XX. Possible nitrogen nucleophiles include ammonia, which leads directly without further release to the compounds of the XX type, azides such as sodium azide, which has to be subsequently reduced to establish the amino function, for which triphenylphosphine (Bioorg. Med. Chem. Lett. 2925, 2002) or noble metal catalysts such as palladium or platinum in the presence of hydrogen are options (J. Med. Chem. 5005, 2002), phthalimide, which has to be treated subsequently with hydrazine to release the amino function (J. Med. Chem. 1315, 2004), or urotropin, which has to be treated with acid, preferably hydrochloric acid, to release the amino function (Synthesis 2145, 2003). The R1, R2, R3 and R9 radicals are each as defined in formula I, and Y is a good leaving group such as chloride, bromide, mesylate or tosylate, and may also be —OH here, which is activated "in situ" to give a good leaving group, which is then subsequently substituted by one of the abovementioned nitrogen nucleophiles (Chem. Pharm. Bul 1493, 1989; Bioorg. Med. Chem. Lett. 2463, 2004).

A further route to amines of the XX type is shown in scheme 7.

Scheme 7:

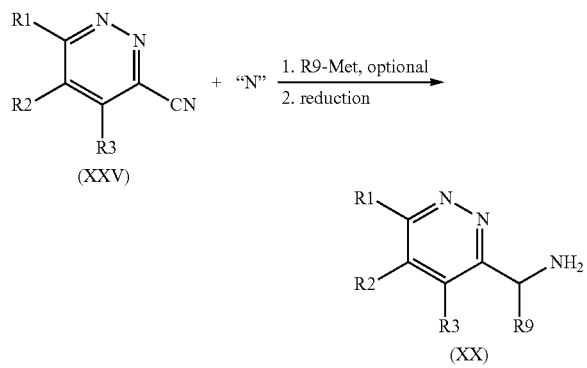

Proceeding from 3-cyanopyridazines of the XXV type, the nitrile function is reduced with reducing agents such as hydrogen in the presence of metal catalysts such as palladium or Raney nickel to give the amines of the XX type. When the nitrile function is reacted before the reduction with organometallic reagents such as Grignard or organolithium compounds, it is also possible by this route to introduce the R9 substituent. The imines obtained as intermediates as a result can be reduced by sodium borohydride, sodium triacetoxyborohydride or sodium cyanoborohydride to the amines XX. The R1, R2, R3 and R9 radicals are each as defined above. Met is —Li or —MgBr.

Alternatively, it is possible to prepare compounds of the formula I as shown in scheme 8.

Scheme 8:

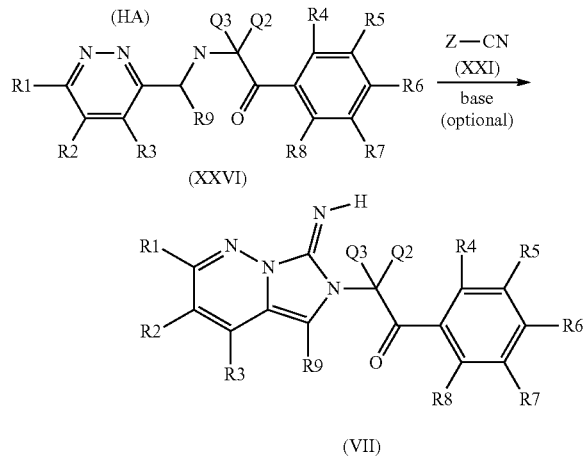

This cyclizes compounds of the formula XXVI—optionally in the form of their salts (HA)—in a solvent such as water, methanol, ethanol, acetic acid, acetonitrile, toluene or suitable mixtures of these solvents, preferably toluene, in the presence of a base, preferably Hünig's base, with a cyano source XXI, preferably cyanogen bromide, to give the desired imidazopyridazines. The R1 to R9, Q2, Q3 and Z radicals are each as defined above.

Compounds of the formula XXVI are obtained according to scheme 9, by reacting amines of the formula XX with acetophenone derivatives of the formula II type. This is preferably done in solvents such as DMF, tetrahydrofuran (THF) or acetonitrile, preferably in THF. Useful bases include Hürig's base, lithium hexamethyldisilazide or potassium carbonate, preferably lithium hexamethyldisilazide. The radicals are each as defined above.

Scheme 9:

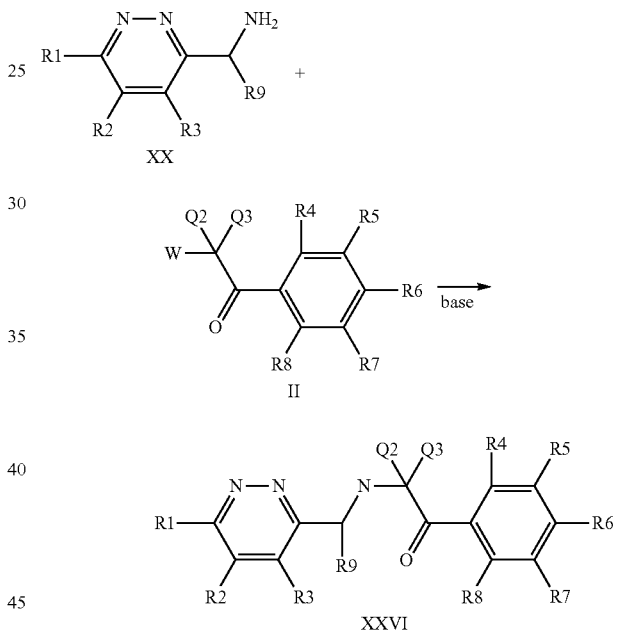

Alternatively, compounds of the formula XXVI according to scheme 10 can be reacted with isothiocyanates of the formula XXII type to give the thioureas XXVII. These are subsequently treated with a "sulfur activator" such as mercury oxide, methyl iodide or ethyl bromoacetate, such that they cyclize directly to give compounds of the formula I type. The radicals are each as defined above.

Scheme 10:

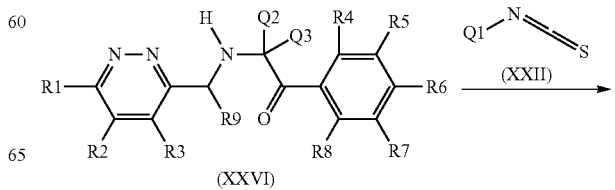

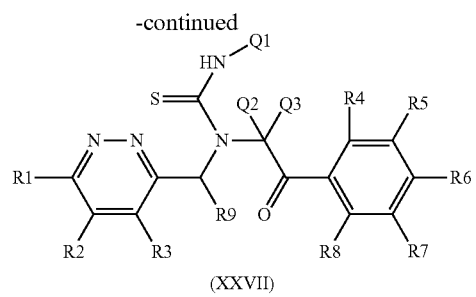

(XXVII)

sulfur activator ↓

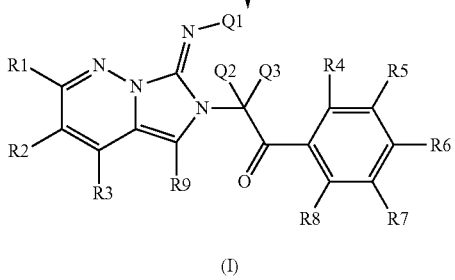

(I)

Some of the compounds of the formula I can also occur in isomeric forms, in which case Q1 in the partial formula of formula I below may either have (E) or (Z) configuration:

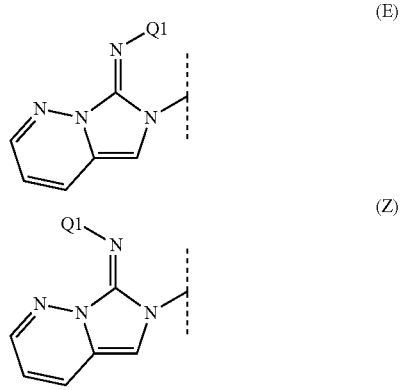

A compound of the formula I prepared according to scheme 1, or a suitable precursor of the formula I which, owing to its chemical structure, occurs in enantiomeric forms, can be separated into the pure enantiomers by salt formation with enantiomerically pure acids or bases, chromatography on chiral stationary phases or derivatization by means of chiral enantiomerically pure compounds such as amino acids, separation of the diastereomers thus obtained, and elimination of the chiral auxiliary groups (process f)), or the compound of the formula I prepared according to scheme 1 can either be isolated in free form or, in the case of the presence of acidic or basic groups, converted to physiologically compatible salts (process e)).

Acidic or basic products of the compound of the formula I may be in the form of their salts or in free form. Pharmacologically acceptable salts are preferred, for example alkali metal or alkaline earth metal salts or hydrochlorides, sulfates, hemisulfates, methylsulfonates, p-toluenesulfonates, all possible phosphates, and salts of amino acids, natural bases or carboxylic acids such as lactates, citrates, tartrates, acetates, adipates, fumarates, gluconates, glutamates, maleates or pamoates.

Physiologically tolerated salts are prepared from compounds of the formula I capable of salt formation, including their stereoisomeric forms, in process step e) in a manner known per se. If compounds of the formula I contain acidic functionality, stable alkali metal, alkaline earth metal or optionally substituted ammonium salts can be formed with basic reagents such as hydroxides, carbonates, bicarbonates, alkoxides, and ammonia or organic bases, for example trimethyl- or triethylamine, ethanolamine, diethanolamine or triethanolamine, trometamol or else basic amino acids, for instance lysine, ornithine or arginine. Basic groups of the compounds of the formula I form acid addition salts with acids. Suitable for this purpose are both inorganic and organic acids such as hydrochloric or hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid.

In process step f), the compound of the formula I, if it occurs as a mixture of diastereomers or enantiomers or results as mixtures thereof in the chosen synthesis, is separated into the pure stereoisomers either by chromatography on an optionally chiral support material or, if the racemic compound of the formula I is capable of salt formation, it is also possible to carry out a fractional crystallization of the diastereomeric salts formed with an optically active base or acid as auxiliary. Examples of suitable chiral stationary phases for thin-layer or column chromatographic separation of enantiomers are modified silica gel supports (called Pirkle phases) and high molecular weight carbohydrates such as triacetylcellulose. For analytical purposes it is also possible to use gas chromatographic methods on chiral stationary phases after appropriate derivatization known to the skilled worker. To separate enantiomers of the racemic carboxylic acids, the diastereomeric salts of differing solubility are formed with an optically active, usually commercially available, base such as (−)-nicotine, (+)- and (−)-phenylethylamine, quinine bases, L-lysine or L- and D-arginine, the less soluble component is isolated as solid, the more soluble diastereomer is deposited from the mother liquor, and the pure enantiomers are obtained from the diastereomeric salts obtained in this way. It is possible in the same way in principle to convert the racemic compounds of the formula I which contain a basic group such an amino group, with optically active acids such as (+)-camphor-10-sulfonic acid, D- and L-tartaric acid, D- and L-lactic acid, and (+) and (−)-mandelic acid, into the pure enantiomers. It is also possible to convert chiral compounds containing alcohol or amine functions with appropriately activated or, where appropriate, N-protected enantiopure amino acids into the corresponding esters or amides, or conversely chiral carboxylic acids with carboxy-protected enantiopure amino acids into the amides or with enantiopure hydroxy carboxylic acids such as lactic acid into the corresponding chiral esters. The chirality of the amino acid or alcohol residue which has been introduced in enantiopure form can then be utilized to separate the isomers by carrying out a separation of the diastereomers which are now available by crystallization or chromatography on suitable stationary phases, and then eliminating the included chiral moiety again by suitable methods.

A further possibility with some of the inventive compounds is to prepare the framework structures using diastereomerically or enantiomerically pure starting materials. It is thus possible also to employ other or simplified processes for purifying the final products. These starting materials have previously been prepared enantiomerically or diastereomerically pure by processes known from the literature. This may mean in particular that either enantioselective processes are employed in the synthesis of the basic structures, or else a separation of enantiomers (or diastereomers) is carried out at an early stage of the synthesis and not at the stage of the final products. A simplification of these separations can likewise be achieved by proceeding in two or more stages.

The invention also relates to medicaments having an effective content of at least one compound of the formula I and/or a physiologically tolerated salt of the compound of the formula I and/or an optionally stereoisomeric form of the compound of the formula I, together with a pharmaceutically suitable and physiologically tolerated carrier, additive and/or other active ingredients and excipients.

Owing to the pharmacological properties, the compounds of the invention are suitable for example for the prophylaxis, secondary prevention and therapy of all disorders which can be treated by inhibition of the protease-activated receptor 1 (PAR1). Thus, the compounds of the invention are suitable both for a prophylactic and a therapeutic use on humans. They are suitable both for acute treatment and for long-term therapy. The compounds of the formula I can be employed in patients suffering from impairments of well being or diseases associated with thromboses, embolisms, hypercoagulability, fibrotic changes or inflammatory disorders. These include myocardial infarction, angina pectoris and all other types of acute coronary syndrome, stroke, peripheral vascular disorders, deep vein thrombosis, pulmonary embolism, embolic or thrombotic events caused by cardiac arrhythmias, cardiovascular events such as restenosis following revascularization, angioplasty and similar procedures such as stent implantations and bypass operations. The compounds of the formula I can further be employed in all procedures leading to contact of blood with foreign surfaces, such as for dialysis patients and patients with indwelling catheters. Compounds of the formula I can be employed in order to reduce the risk of thrombosis following surgical procedures such as knee and hip joint operations.

Compounds of the formula I are suitable for the treatment of patients with disseminated intravascular coagulation, sepsis and other intravascular events associated with inflammation.

The compounds of the formula I are further suitable for the prophylaxis and treatment of patients with atherosclerosis, diabetes and the metabolic syndrome and the sequelae thereof. Impairments of the hemostatic system (for example fibrin deposits) have been implicated in mechanisms leading to tumor growth and tumor metastasis, and in inflammatory and degenerative articular disorders such as rheumatoid arthritis and arthrosis. Compounds of the formula I are suitable for retarding or preventing such processes.

Further indications for the use of the compounds of the formula I are fibrotic changes in the lung such as chronic obstructive pulmonary disease, adult respiratory distress syndrome (ARDS) and of the eye such as fibrin deposits following eye operations. Compounds of the formula I are also suitable for the prevention and/or treatment of scarring.

The medicaments of the invention can be administered by oral, inhalational, rectal or transdermal administration or by subcutaneous, intraarticular, intraperitoneal or intravenous injection. Oral administration is preferred. Coating of stents with compounds of the formula I and other surfaces which come into contact with blood in the body is possible.

The invention also relates to a process for manufacturing a medicament, which comprises making a suitable dosage form from at least one compound of the formula I with a pharmaceutically suitable and physiologically tolerated carrier and, where appropriate, further suitable active ingredients, additives or excipients.

Suitable solid or pharmaceutical formulations are, for example, granules, powder, coated tablets, tablets, (micro) capsules, suppositories, syrups, solutions, suspensions, emulsions, drops or injectable solutions, and products with protracted release of active ingredient, in the production of which customary aids such as carriers, disintegrants, binders, coating agents, swelling agents, glidants or lubricants, flavorings, sweeteners and solubilizers are used. Excipients which are frequently used and which may be mentioned are magnesium carbonate, titanium dioxide, lactose, mannitol and other sugars, talc, milk protein, gelatin, starch, cellulose and its derivatives, animal and vegetable oils such as fish liver oil, sunflower, peanut or sesame oil, polyethylene glycol and solvents such as, for example, sterile water and monohydric or polyhydric alcohols such as glycerol.

The pharmaceutical products are preferably manufactured and administered in dosage units, where each unit comprises as active ingredient a particular dose of the compound of the invention of the formula I. In the case of solid dosage units such as tablets, capsules, coated tablets or suppositories, this dose can be up to about 1000 mg, but preferably about 50 to 300 mg and, in the case of injection solutions in ampoule form, up to about 300 mg but preferably about 10 to 100 mg.

The daily doses indicated for the treatment of an adult patient weighing about 70 kg are, depending on the activity of the compound of formula I, from about 2 mg to 1000 mg of active ingredient, preferably about 50 mg to 500 mg. However, in some circumstances, higher or lower daily doses may also be appropriate. The daily dose can be administered either by a single administration in the form of a single dosage unit or else a plurality of smaller dosage units or by multiple administration of divided doses at particular intervals.

Compounds of the formula I can be administered both as monotherapy and in combination or together with all antithrombotics (anticoagulants and platelet aggregation inhibitors), thrombolytics (plasminogen activators of every type), other substances having profibrinolytic activity, antihypertensives, regulators of blood glucose, lipid-lowering agents and antiarrhythmics. Suitable platelet aggregation inhibitors in this connection are cyclooxygenase 1 inhibitors such as aspirin, irreversible $P2Y_{12}$ antagonists such as clopidogrel or prasugrel, reversible $P2Y_{12}$ antagonists such as cangrelor or AZD6140 and thromboxane $A_2$/prostaglandin $H_2$ antagonists such as terutroban. It has been possible to show additive effects of PAR1 blockade in combination with $P2Y_{12}$ blockade for example (Eur. Heart J. 2007, 28, Abstract Supplement, 188).

EXAMPLES

End products were generally characterized by a chromatography/mass spectroscopy method (LCUV/ESI-MS coupling) and $^1$H NMR. The compounds are described by reporting the corresponding retention time in the ion current (LC-MS Rt) and the corresponding M+H$^+$ signal in the case of positive ionization in the corresponding mass spectrum. When no M+H$^+$ mass signal could be obtained, the $^1$H NMR data were reported as an alternative. Abbreviations used are either explained or correspond to the usual conventions. Silica gel separations were carried out manually (flash chromatography) or supported by semiautomatic cartridge systems such as Companion (CombiFlash) or Flashmaster II (Jones Chromatography). Unless stated otherwise, chromatographic separations were carried out on silica gel with ethyl acetate/heptane, dichloromethane/ethanol or dichloromethane/methanol mixtures as the eluent. Solvents were evaporated generally under reduced pressure at from 35° C. to 45° C. on a rotary evaporator, which is referred to by phrases such as "freed of the solvent", "concentrated", "concentrated by rotary evaporation", "dried", "solvent removed or drawn off" or similar expressions. Unless stated otherwise, the LCUV/MS analyses were carried out under the following conditions:

System: Agilent 1100 HPLC-System coupled to 1100 LC/MSD

Column: YMC J'shere ODS H80 20×2.1 mm, packing material 4 μm

Eluent: ACN:H$_2$O+0.05% TFA (flow rate 1 ml/min)

Gradient: 4:96 (0 min)➔95:5 (2 min)➔95:5 (2.4 min)➔4:96 (2.45 min)

Ionization: ESI$^+$

Preparative HPLC with reversed-phase (RP) silica gel was carried out by the following methods:

Method A, standard method if no other method is mentioned in the text.

Column: Merck (Darmstadt, Deutschland) Purosphere® RP18 25×250 mm, 10 μm

Eluent: ACN:H$_2$O+0.05% TFA (flow rate 25 ml/min)

Gradient: 10:90 (0 min)➔90:10 (40 min)

Method B

Column: Merck Purosphere® RP18 25×250 mm, 10 μm

Eluent: ACN:H$_2$O+0.05% TFA (flow rate 25 ml/min)

Gradient: 0:100 (0 min)➔0:100 (5 min)➔20:80 (20 min)

Method C

Column: Agilent Prep-C18, 30×250 mm, 10 μm

Eluent: ACN:H$_2$O+0.05% TFA (flow rate 75 ml/min)

Gradient: 10:90 (0 min)➔90:10 (12.5 min)➔90:10 (15 min)➔10:90 (15.5 min)➔10:90 (17.5 min)

The reactions took place in standard reaction apparatus such as single-neck or multineck flasks, which, unless stated otherwise, according to the need, had a capacity of from 5 ml to 2000 ml and, as required, were equipped with a septum, stopper, condenser, stirrer or other equipment. Unless mentioned otherwise, all reactions took place under argon as protective gas and were stirred with magnetic stirrers.

Microwave reactions were carried out in the Emrys Optimizer from Personal Chemistry in vessels of capacity from 0.5 to 10 ml according to the need.

| Abbreviations used: | |
|---|---|
| abs. | absolute |
| ACN | acetonitrile |
| Boc | butoxycarbonyl |
| DCM | dichloromethane |
| DIPEA | N,N-diisopropylethylamine (Hünig's base) |
| DMF | dimethylformamide |
| DMSO | dimethyl sulfoxide |
| EA | ethyl acetate |
| HPLC | high-performance liquid chromatography |
| LC-MS Rt | retention time of the compound in the ion current |
| LCUV/MS | ultraviolet liquid chromatography/mass spectrometry |
| MeOH | methanol |
| RT | room temperature (20° C. to 25° C.) |
| TFA | trifluoroacetic acid |
| THF | tetrahydrofuran |

Example 1

N-{3-[2-(2,3-Diethoxy-7-iminoimidazo[1,5-b]pyridazin-6-yl)acetyl]-5-pentamethylsulfanylphenyl}acetamide as trifluoroacetic acid salt

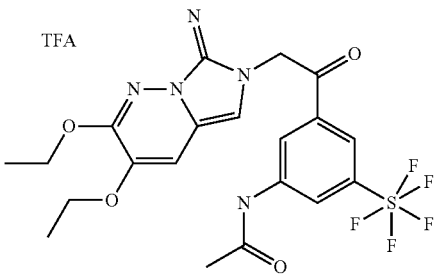 [SMILES: CCOc1cc2cn(CC(=O)c3cc(NC(C)=O)cc(S(F)(F)(F)(F)F)c3)c(=N)n2nc1OCC]

a) 3-Nitro-5-pentafluorosulfanylbenzoic acid

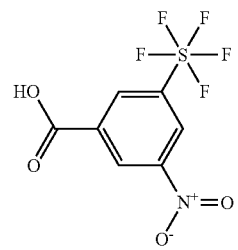 [SMILES: O=C(O)c1cc([N+](=O)[O-])cc(S(F)(F)(F)(F)F)c1]

3-Pentafluorosulfanylbenzoic acid (5.0 g) was dissolved in fuming nitric acid (20 ml) and stirred at RT with exclusion of moisture. Then concentrated sulfuric acid (3 ml) was added and the mixture was stirred at 75° C. After stirring at 75° C. for 5 h, further sulfuric acid (1.5 ml) was added and, after stirring at 75° C. for 2 h, left to stand overnight. Then the mixture was added to ice-water and stirred for 2 h. The precipitate formed was filtered off with suction and dried under high vacuum. 4.2 g of 3-pentafluorosulfanyl-5-nitrobenzoic acid were obtained. A further 900 mg were obtained from the mother liquor after extracting three times with methylene chloride, drying the combined methylene chloride phases over magnesium sulfate and concentrating the solvent. The precipitate was used in the next stage without further purification.

$^1$H NMR (400 MHz, DMSO-d$_6$) [ppm]: 8.82 (1H); 8.80 (1H); 8.62 (1H)

b) N-Methoxy-N-methyl-5-nitro-3-pentafluorosulfanylbenzamide

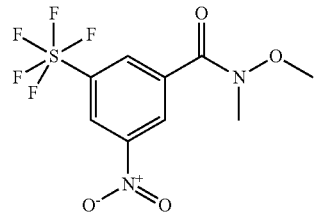 [SMILES: CON(C)C(=O)c1cc([N+](=O)[O-])cc(S(F)(F)(F)(F)F)c1]

3-Nitro-5-pentafluorosulfanylbenzoic acid (4.0 g) was dissolved in thionyl chloride (25 ml) while stirring and kept under reflux with exclusion of moisture for 10 h. After standing overnight, excess thionyl chloride was removed under reduced pressure at RT, and the resulting residue was dissolved in dichloromethane (50 ml) and admixed with N,O- dimethylhydroxylamine hydrochloride (1.25 g) and diethylisopropylamine (1.66 g) while stirring. After stirring at RT for 1 h, the mixture was concentrated under reduced pressure, and the residue was dissolved in ethyl acetate and washed 5 times with water. The organic phase was dried over magnesium sulfate, filtered and concentrated. The resulting crude product (4.2 g) was used directly in the next stage. LC-MS Rt: 1.50 min [M+H]$^+$:337.0 c) 3-Amino-N-methoxy-N-methyl-5-pentafluorosulfanylbenzamide

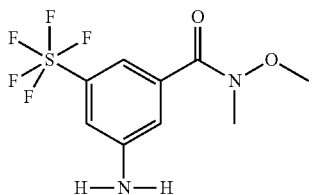 [SMILES: CON(C)C(=O)c1cc(N)cc(S(F)(F)(F)(F)F)c1]

N-Methoxy-N-methyl-5-nitro-3-pentafluorosulfanylbenzamide (4.2 g) was dissolved in methanol (120 ml), and Raney nickel (about 700 mg) was added. With a hydrogen balloon attached, hydrogenation was effected on a magnetic stirrer. After 5 h, the catalyst was filtered off and washed with methanol. The filtrate was concentrated under reduced pressure and the residue was purified by means of preparative HPLC. The product-containing fractions were combined, freed of the acetonitrile, basified with sodium hydrogencarbonate solution and extracted three times with ethyl acetate. The combined extracts were dried over magnesium sulfate, filtered and concentrated. 1.73 g of the desired compound were obtained.

LC-MS Rt: 1.27 min [M+H]$^+$:307.0 d) 3-Acetylamino-N-methoxy-N-methyl-5-(pentafluorosulfanyl)benzamide

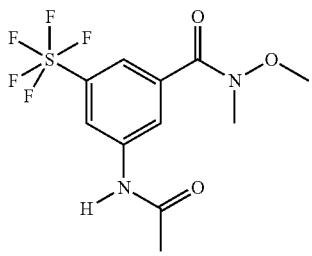 [SMILES: CON(C)C(=O)c1cc(NC(C)=O)cc(S(F)(F)(F)(F)F)c1]

3-Amino-N-methoxy-N-methyl-5-pentafluorosulfanylbenzamide (1.2 g) was dissolved in methylene chloride (15 ml), and triethylamine (0.7 ml) followed by acetic anhydride (1.75 ml) were added while stirring with exclusion of moisture. After stirring at RT for 3 h, water and saturated sodium hydrogencarbonate solution were added, the phases were separated and the methylene chloride phase was washed three times more with water, dried over magnesium sulfate, filtered and concentrated. The resulting product (1.3 g) was used in the next stage without further purification. LC-MS Rt: 1.26 min [M+H]$^+$:349.0 e) N-[3-Acetyl-5-(pentafluorosulfanyl)phenyl]acetamide

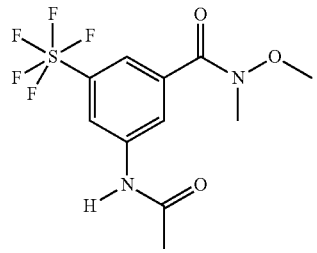 [SMILES: CON(C)C(=O)c1cc(NC(C)=O)cc(S(F)(F)(F)(F)F)c1]

3-Acetylamino-N-methoxy-N-methyl-5-(pentafluorosulfanyl)benzamide (1.2 g) was dissolved in absolute THF (30 ml) and stirred at 0° C. with lithium hexamethyldisilazide (721 µl; density: 0.8 g/1; 23% in tent-butyl methyl ether) for 30 min. At 0° C., methylmagnesium bromide (2.87 ml, 3 M in diethyl ether) was then added dropwise while stirring. After stirring at RT for 2.5 h, further methylmagnesium bromide (1 ml, 3 M in diethyl ether) was added and the mixture was stirred again for 2.5 h. For workup, 1 N hydrochloric acid was added dropwise while cooling with ice, followed by water and ethyl acetate. The organic phase was removed and the water phase was extracted twice more with ethyl acetate. The combined ethyl acetate phases were dried over sodium sulfate, filtered and concentrated. The crude product (1.03 g) was combined with a crude product prepared in the same way (75 mg) and purified using silica gel with dichloromethane-methanol as the eluent. 860 mg of the desired compound were obtained. LC-MS Rt: 1.34 min [M+H]$^+$:304.0 f) N-[3-(2-Bromoacetyl)-5-(pentafluorosulfanyl)phenyl]acetamide

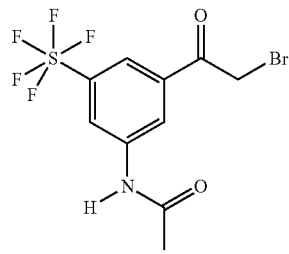 [SMILES: CC(=O)Nc1cc(C(=O)CBr)cc(S(F)(F)(F)(F)F)c1]

N-[3-Acetyl-5-(pentafluorosulfanyl)phenyl]acetamide (859 mg) was dissolved in a mixture of methanol (10 ml) and THF (10 ml) and phenyltrimethylammonium tribromide (1.065 g) was added in portions while stirring. After stirring at RT for 2 h, the mixture was heated to 40° C. for a further 3 h. After cooling, the reaction mixture was added to 2 N sulfuric acid and the aqueous phase was extracted 3 times with ethyl acetate. The combined extracts were dried over sodium sulfate, filtered and concentrated. The crude product was purified using silica gel with ethyl acetate/heptane as the eluent. 480 mg of the desired compound were obtained.

LC-MS Rt: 1.47 min [M+H]$^+$:382.0 g) 3,4-Diethoxy-6-methyl-pyridazine 1-oxide

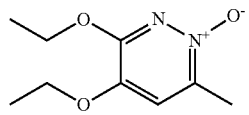

3-Methoxy-6-methyl-4-nitropyridazine 1-oxide (2 g) was initially charged in ethanol (100 ml) at RT. Thereafter, solid sodium ethoxide (1.4 g) was added in portions while stirring. After stirring at 55° C. for 1.5 h, the reaction mixture was cooled to RT and admixed with water, and the aqueous phase was extracted 3 times with dichloromethane. The combined organic phases were dried over sodium sulfate, filtered and concentrated. The crude product was purified by means of preparative HPLC. The clean, product-containing fractions were combined, freed of the acetonitrile and extracted three times with dichloromethane. The combined organic phases were dried over sodium sulfate, filtered and concentrated. 176 mg of the desired product were obtained. The aqueous phase was freeze-dried to obtain 781 mg of the desired product. To obtain further product, the contaminated fractions from the chromatography were combined and freeze-dried. The residues were purified again by means of preparative HPLC, and the clean product was isolated as described above. A further 130 mg of product were obtained.

LC-MS Rt: 0.72 min [M+H]$^+$:199.1 h) (5,6-Diethoxypyridazin-3-yl)methanol

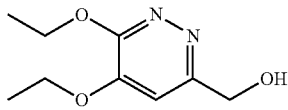

3,4-Diethoxy-6-methylpyridazine 1-oxide (1.44 g) was initially charged in dichloromethane (50 ml) and admixed dropwise at RT with trifluoroacetic anhydride (2.5 ml). After 2.5 h, the mixture was concentrated to dryness and the residue was taken up with ethanol and saturated potassium carbonate solution. After stirring at RT for 4 h, the mixture was concentrated to dryness again and the residue was admixed with water and dichloromethane. Removal of the organic phase was followed by extraction twice more with dichloromethane, and the combined organic phases were dried over magnesium sulfate, filtered and concentrated. The residue was purified twice using silica gel with dichloromethane/methanol as the eluent. The product-containing fractions were combined and dried. 716 mg of the desired product were obtained.

LC-MS Rt: 0.57 min [M+H]$^+$:199.1 i) 5,6-Diethoxypyridazin-3-ylmethyl methanesulfonate

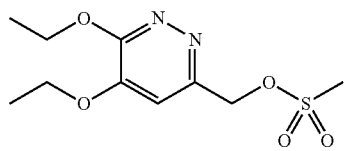 [SMILES: CCOc1cc(COS(C)(=O)=O)nnc1OCC]

(5,6-Diethoxypyridazin-3-yl)methanol (716 mg) was initially charged in dichloromethane (35 ml), and methanesulfonic anhydride (1.7 g dissolved in 5 ml of dichloromethane) and triethylamine (0.8 ml) were successively added dropwise while stirring. After 2 h, the mixture was admixed with water and saturated sodium hydrogencarbonate solution and extracted three times with dichloromethane. The combined organic phases were dried over sodium sulfate, filtered and concentrated. 1.1 g of the desired compound were obtained.

LC-MS Rt: 0.98 min [M+H]$^+$:277.0 j) C-(5,6-Diethoxypyridazin-3-yl)methylamine

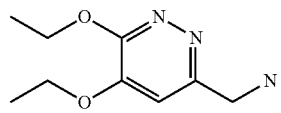

5,6-Diethoxypyridazin-3-ylmethyl methanesulfonate (620 mg) was dissolved in methanol (10 ml) and added dropwise while cooling with ice to an ammonia solution (16 ml; 7N in methanol). After being stirred for 6 h and left to stand overnight, the solvent was drawn off and the residue was purified by means of preparative HPLC. The product-containing fractions were combined, freed of the acetonitrile and freeze-dried. 305 mg of the desired product were obtained.

LC-MS Rt: 0.62 min [M+H]$^+$:198.1 k) 2,3-Diethoxyimidazo[1,5-b]pyridazin-7-ylamine as trifluoroacetic acid salt

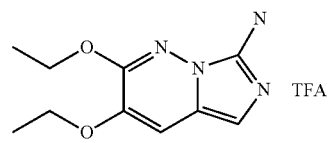 [SMILES: CCOc1cc2cnc(N)n2nc1OCC]

C-(5,6-Diethoxypyridazin-3-yl)methylamine (296 mg) was initially charged in a mixture of ethanol (15 ml) and water (3 ml) while stirring at RT. Thereafter, cyanogen bromide (0.8 ml; 5M in acetonitrile) was added dropwise. After being stirred for 6 h and left to stand overnight, further cyanogen bromide (0.8 ml) was added. After being stirred for 9 h and standing overnight, the solvent was drawn off and the residue was purified by means of preparative HPLC. The product-containing fractions were combined, freed of the acetonitrile and freeze-dried. The still-contaminated product was separated for further purification using silica gel with dichloromethane-methanol as the eluent. 99 mg of the desired compound were obtained.

LC-MS Rt: 0.83 min [M+H]$^+$:223.1 l) N-{3-[2-(2,3-Diethoxy-7-iminoimidazo[1,5-b]pyridazin-6-yl)acetyl]-5-pentamethylsulfanylphenyl}acetamide as trifluoroacetic acid salt 2,3-Diethoxyimidazo[1,5-b]pyridazin-7-ylamine trifluoroacetic acid salt (22 mg) was initially charged in absolute DMF (2.5 ml) at RT while stirring, and admixed with diisopropylethyl-amine (5 µl). Thereafter, N-[3-(2-bromoacetyl)-5-(pentafluorosulfanyl)phenyl]acetamide (25 mg), dissolved in absolute DMF (1 ml), was added dropwise. After being stirred for 4 h and left to stand overnight, the solvent was drawn off and the residue was purified by means of preparative HPLC. The product-containing fractions were combined, freed of the acetonitrile and freeze-dried. 24 mg of the desired compound were obtained.

LC-MS Rt: 1.23 min [M+H]$^+$:524.0

Example 2

1-(3-tert-Butyl-4-methoxy-5-morpholin-4-ylphenyl)-2-(7-imino-2,3-dimethoxyimidazo-[1,5-b]pyridazin-6-yl)ethanone as trifluoroacetic acid salt

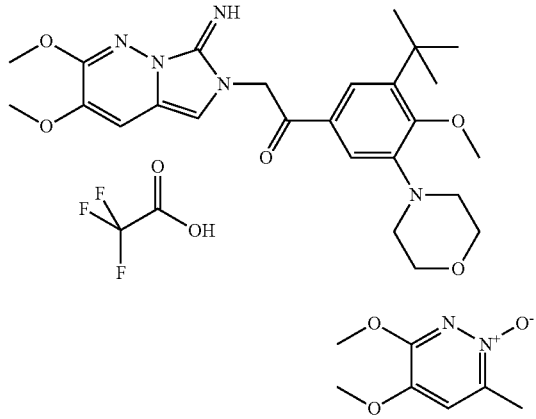

a) 3,4-Dimethoxy-6-methylpyridazine 1-oxide

3-Methoxy-6-methyl-4-nitropyridazine 1-oxide (1 g) was converted and worked up analogously to example 1 g). Chromatography of the crude product was unnecessary. The solvent used was methanol (30 ml), and the base sodium methoxide (as 30% solution in methanol, 1.1 ml). Yield: 900 mg
LC-MS Rt: 0.29 min $[M+H]^+$:171.1 b) (5,6-Dimethoxypyridazin-3-yl)methyl methanesulfonate

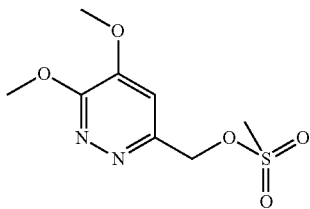 [SMILES: COc1cc(COS(C)(=O)=O)nnc1OC]

3,4-Dimethoxy-6-methylpyridazine 1-oxide (880 mg) was converted to the title compound analaogously to the sequence of example 1h-1i). Yield: 690 mg
LC-MS Rt: 0.71 min $[M+H]^+$:249.0 c) C-(5,6-Dimethoxypyridazin-3-yl)methylamine trifluoroacetic acid salt

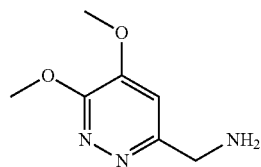

(5,6-Dimethoxypyridazin-3-yl)methyl methanesulfonate (690 mg) was dissolved in chloroform (10 ml) and added dropwise at 0° C. to a urotropin solution (390 mg in 20 ml of chloroform). Thereafter, the cooling bath was removed, and the mixture was stirred at RT for 1.5 h and then at 40° C. for 5 h. After standing over the weekend, it was stirred again at 40° C. for 5 h. Then the solvent was drawn off, and the residue was taken up with methanol (40 ml), concentrated hydrochloric acid (1.2 ml) was added and the mixture was stirred at RT for 30 min. Then it was dried, and the residue was taken up with water/acetonitrile and freeze-dried. 1.2 g of the crude product were obtained. 184 mg thereof were purified by means of preparative HPLC. The product-containing fractions were combined, freed of the acetonitrile and freeze-dried. 40 mg of the desired compound were obtained.
LC-MS Rt: 0.20 min $[M+H]^+$:170.1 d) 2,3-Dimethoxyimidazo[1,5-b]pyridazin-7-ylamine trifluoroacetic acid salt

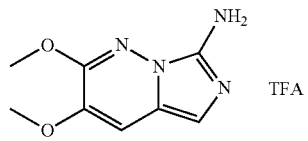

C-(5,6-Dimethoxypyridazin-3-yl)methylamine trifluoroacetic acid salt (37 mg) was initially charged in a mixture of ethanol and water (3.75/0.75 ml) while stirring at RT. Thereafter, cyanogen bromide solution (0.1 ml; 5M in ACN) was cautiously added dropwise and the mixture was stirred at RT for 3 h. Then further cyanogen bromide solution (0.1 ml) was added and the mixture was left to stand overnight. After again adding cyanogen bromide solution (0.1 ml), the mixture was stirred for 4 h, left to stand over the weekend and then heated to 40° C. for 2 h. Subsequently, the solvent was drawn off and the residue was purified by means of preparative HPLC. The product-containing fractions were combined, freed of the acetonitrile and freeze-dried. 18 mg of the desired compound were obtained.
LC-MS Rt: 0.64 min $[M+H]^+$:195.1 e) 1-(3-tert-Butyl-4-methoxy-5-morpholin-4-ylphenyl)-2-(7-imino-2,3-dimethoxy-imidazo[1,5-b]pyridazin-6-yl)ethanone as trifluoroacetic acid salt 2,3-Dimethoxyimidazo[1,5-b]pyridazin-7-ylamine trifluoroacetic acid salt (15 mg) and 2-bromo-1-(3-tert-butyl-4-methoxy-5-morpholin-4-ylphenyl)ethanone (20 mg; prepared as described in WO 2004/078721) were reacted with one another, worked up and purified analogously to example 11). 27 mg of the title compound were obtained.
LC-MS Rt: 1.28 min $[M+H]^+$:484.4

Example 3

1-(3-tert-Butyl-4-methoxy-5-morpholin-4-ylphenyl)-2-(2,3-diethoxy-7-iminoimidazo-[1,5-b]pyridazin-6-yl)ethanone as trifluoroacetic acid salt

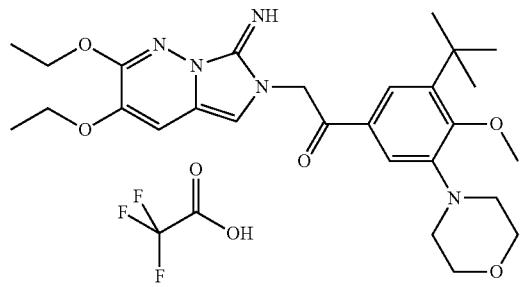

2,3-Diethoxyimidazo[1,5-b]pyridazin-7-ylamine trifluoroacetic acid salt [example 1k), 15 mg] and 2-bromo-1-(3-tert-butyl-4-methoxy-5-morpholin-4-ylphenyl)ethanone (27 mg; prepared as described in WO 2004/078721) were reacted with one another, worked up and purified analogously to example 11). 27 mg of the title compound were obtained.
LC-MS Rt: 1.38 min $[M+H]^+$:512.3

Example 4

1-(3-tert-Butyl-4-methoxy-5-morpholin-4-ylphenyl)-2-[7-imino-2-methoxy-3-(2,2,2-trifluoroethoxy)imidazo[1,5-b]pyridazin-6-yl]ethanone as trifluoroacetic acid salt

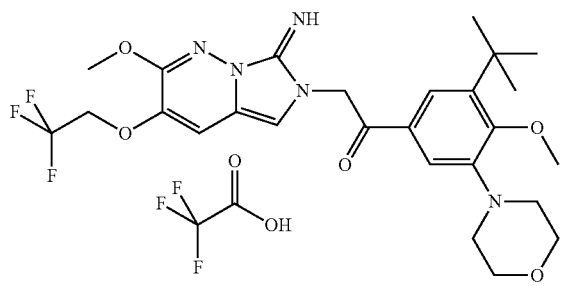

a) 3-Methoxy-6-methyl-4-(2,2,2-trifluoroethoxy)pyridazine 1-oxide

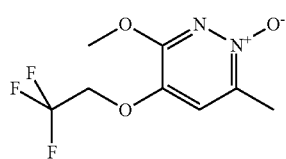 [SMILES: COc1n[n+]([O-])c(C)cc1OCC(F)(F)F]

2,2,2-Trifluoroethanol (3 ml) was initially charged at RT and admixed with sodium hydride (403 mg) in portions while cooling with ice. Thereafter, the reaction mixture was heated to 55° C. for 2 h and then 3-methoxy-6-methyl-4-nitropyridazine 1-oxide solution (500 mg, dissolved in 3 ml of 2,2,2-trifluoroethanol) was added dropwise. After stirring at RT for 1 h, the mixture was heated to 55° C. for 2.5 h. After standing at RT overnight, the mixture was admixed with water and DCM. After removing the DCM phase, the aqueous phase was extracted three times with DCM and the combined DCM phases were dried over sodium sulfate, filtered and concentrated. 571 mg of the title compound were obtained.
LC-MS Rt: 0.80 min [M+H]⁺:239.1 b) C-[6-Methoxy-5-(2,2,2-trifluoroethoxy)pyridazin-3-yl]methylamine as trifluoroacetic acid salt

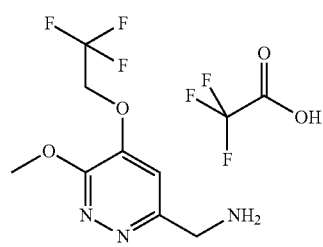

3-Methoxy-6-methyl-4-(2,2,2-trifluoroethoxy)pyridazine 1-oxide (570 mg) was converted to the title compound analogously to the sequence of example 1 h-1j). 210 mg of the title compound were obtained. LC-MS Rt: 0.64 min [M+H]⁺: 238.1 c) 2-Methoxy-3-(2,2,2-trifluoroethoxy)imidazo[1,5-b]pyridazin-7-ylamine as hydrobromide

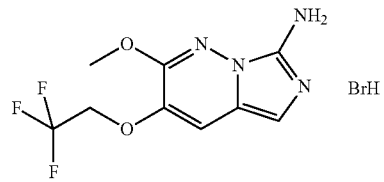 [SMILES: COc1nn2c(N)ncc2cc1OCC(F)(F)F ; Br]

C-[6-Methoxy-5-(2,2,2-trifluoroethoxy)pyridazin-3-yl]methylamine as trifluoroacetic acid salt 204 mg) was initially charged in a mixture of ethanol/water (15/3 ml). Thereafter, cyanogen bromide solution (62 mg dissolved in ethanol/wasser 3.75/0.75 ml) was added dropwise. After stirring at RT for 2 h, the same amount of cyanogen bromide again was added dropwise. After stirring at RT for 4 h, the mixture was left to stand overnight and then stirred for a further 4 h. Subsequently, further cyanogen bromide (60 mg dissolved in ethanol/water 1.88/0.38 ml) was added. After stirring at RT for 3 h, the mixture was left to stand again overnight and then the solvent was drawn off. The residue was purified using silica gel (25 g cartridge, DCM/methanol gradient). The substance-containing fractions were combined and dried. As well as 62 mg of reactant, 20 mg of the title compound were obtained. LC-MS Rt: 0.86 min [M+H]⁺:263.0 d) 1-(3-tert-Butyl-4-methoxy-5-morpholin-4-ylphenyl)-2-[7-imino-2-methoxy-3-(2,2,2-trifluoroethoxy)imidazo[1,5-b]pyridazin-6-yl]ethanone as trifluoroacetic acid salt 2-Methoxy-3-(2,2,2-trifluoroethoxy)imidazo[1,5-b]pyridazin-7-ylamine hydrobromide (18 mg) and 2-bromo-1-(3-tert-butyl-4-methoxy-5-morpholin-4-ylphenyl)ethanone (22 mg; prepared as described in WO 2004/078721) were reacted with one another, worked up and purified analogously to example 11). 31 mg of the title compound were obtained.
LC-MS Rt: 1.39 min [M+H]⁺:552.2

Example 5

2-(2,3-Diethoxy-7-iminoimidazo[1,5-b]pyridazin-6-yl)-1-[3-methylamino-5-(pentafluoro-sulfanyl)phenyl]ethanone as trifluoroacetic acid salt

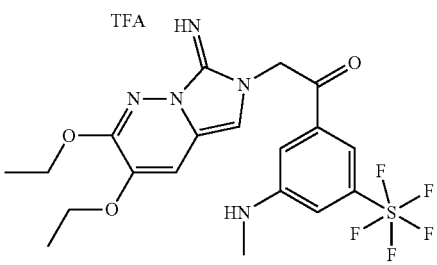 [SMILES: CCOc1cc2cn(CC(=O)c3cc(NC)cc(S(F)(F)(F)(F)F)c3)c(=N)n2nc1OCC]

a) N-Methoxy-N-methyl-3-(pentafluorosulfanyl)-5-(2,2,2-trifluoroacetylamino)benzamide

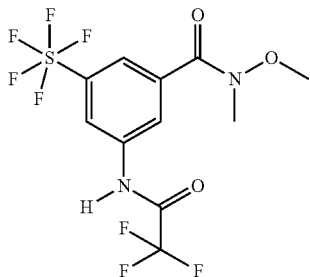 [SMILES: CON(C)C(=O)c1cc(NC(=O)C(F)(F)F)cc(S(F)(F)(F)(F)F)c1]

3-Amino-N-methoxy-N-methyl-5-pentafluorosulfanyl-benzamide [example 1c]; 1.45 g] was dissolved in methylene chloride (15 ml), and triethylamine (0.8 ml) followed by trifluoroacetic anhydride (0.85 ml) were added while stirring with exclusion of moisture. After stirring at RT for 3 h and standing overnight, water and saturated sodium hydrogencarbonate solution were added, the phases were separated and the methylene chloride phase was washed three times with water, dried over magnesium sulfate, filtered and concentrated. The resulting product (1.75 g) was used without further purification in the next stage.

LC-MS Rt: 1.53 min [M+H]$^+$:403.0 b) N-(3-Acetyl-5-pentafluorosulfanylphenyl)-2,2,2-trifluoroacetamide

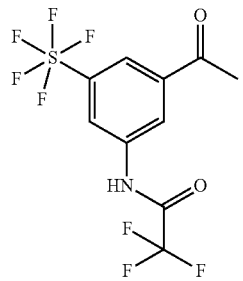 [SMILES: CC(=O)c1cc(NC(=O)C(F)(F)F)cc(S(F)(F)(F)(F)F)c1]

N-Methoxy-N-methyl-3-(pentafluorosulfanyl)-5-(2,2,2-trifluoroacetylamino)benzamide (1.65 g) was dissolved in THF (25 ml). At 0° C., lithium bis(trimethylsilyl)amide (0.9 ml) was added while stirring. After 30 min, methylmagnesium bromide (3.5 ml, 3M in diethyl ether) was added dropwise. After the addition had ended, the ice bath was removed and the mixture was stirred at RT for 2 h. While cooling, 1N hydrochloric acid, water and EA were then added. After removing the organic phase, the aqueous phase was extracted twice more with EA. The combined EA phases were dried with magnesium sulfate, filtered and concentrated. The crude product is a mixture of N-(3-acetyl-5-pentafluorosulfanylphenyl)-2,2,2-trifluoroacetamide and 1-[3-amino-5-(pentafluorosulfanyl)phenyl]ethanone, and so the crude product (1.3 g) was taken up in methylene chloride (60 ml) and admixed with triethylamine (155 µl). Thereafter, trifluoroacetic anhydride (160 µl) was added while stirring. After stirring at RT for 3 h, water and saturated sodium hydrogencarbonate solution were added, the phases were separated and the DCM phase was washed three times more with water. The DCM phase was dried with magnesium sulfate, filtered and concentrated. 1.3 g of the title compound were obtained. LC-MS Rt: 1.61 min [M+H]$^+$:358.0 c) N-[3-Acetyl-5-(pentafluorosulfanyl)phenyl]-2,2,2-trifluoro-N-methylacetamide

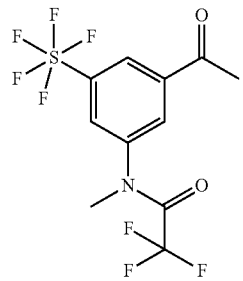 [SMILES: CC(=O)c1cc(N(C)C(=O)C(F)(F)F)cc(S(F)(F)(F)(F)F)c1]

In a microwave insert, N-(3-acetyl-5-pentafluorosulfanylphenyl)-2,2,2-trifluoroacetamide (0.25 g) was dissolved in absolute dimethoxyethane (7.5 ml), powdered potassium carbonate was added and the mixture was admixed with iodomethane (80 µl). Subsequently, the mixture was heated to 100° C. in the microwave for 40 min. Once further N-(3-acetyl-5-pentafluorosulfanylphenyl)-2,2,2-trifluoroacetamide (4×250 mg) had been converted in the manner described, the five batches were worked up together, having been decanted from the potassium carbonate into 1N hydrochloric acid while cooling with ice. After repeatedly washing the potassium carbonate residue with dimethoxyethane, the aqueous phase was extracted five times with ethyl acetate. The combined extracts were dried over magnesium sulfate, filtered and concentrated. The residue was purified by means of preparative HPLC. The product-containing fractions were combined, freed of the acetonitrile and extracted five times with ethyl acetate. The combined extracts were dried over magnesium sulfate, filtered and concentrated. 1.03 g of the desired compound were obtained.

LC-MS Rt: 1.62 min [M+H]$^+$:372.0 d) N-[3-(2-Bromoacetyl)-5-(pentafluorosulfanyl)phenyl]-2,2,2-trifluoro-N-methyl-acetamide

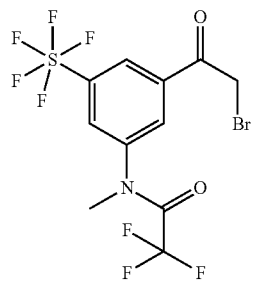 [SMILES: CN(C(=O)C(F)(F)F)c1cc(C(=O)CBr)cc(S(F)(F)(F)(F)F)c1]

N-[3-Acetyl-5-(pentafluorosulfanyl)phenyl]-2,2,2-trifluoro-N-methylacetamide (1.03 g) was dissolved in a mixture of methanol (20 ml) and THF (20 ml). Phenyltrimethylammonium tribromide (1.05 g) was added while stirring. After stirring at RT for 5 h, the mixture was left to stand overnight, then further phenyltrimethylammonium tribromide (100 mg) was added and the mixture was heated to 60° C. for 2 h. After cooling, the reaction mixture was added to 2N sulfuric acid and stirred for 10 min. Then the aqueous phase was extracted three times with EA. The combined organic phases were dried over magnesium sulfate and, after filtering off the desiccant, dried under reduced pressure. 1.2 g of the title compound were obtained, which had sufficient purity for the next reactions.

LC-MS Rt: 1.72 min [M+H]$^+$:449.9 e) 2-Bromo-1-[3-methylamino-5-(pentafluorosulfanyl)phenyl]ethanone

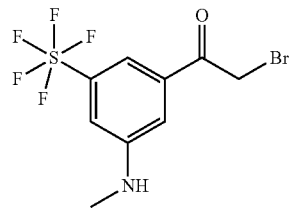 [SMILES: CNc1cc(C(=O)CBr)cc(S(F)(F)(F)(F)F)c1]

N-[3-(2-Bromoacetyl)-5-(pentafluorosulfanyl)phenyl]-2,2,2-trifluoro-N-methylacetamide (O1.075; 1.2 g) was admixed with water (15 ml), and concentrated sulfuric acid (15 ml) was added dropwise while stirring and cooling with ice. The mixture was heated to 80° C. and stirred at this temperature for 7 h. After cooling, the reaction mixture was slowly added to a mixture of 10N sodium hydroxide solution and EA, and the aqueous phase was extracted five times with EA. The combined organic phases were dried over magnesium sulfate and, after filtering off the desiccant under reduced pressure, dried. The residue was purified by means of preparative HPLC. The product fractions, each of them clean, were combined, freed of the acetonitrile under reduced pressure, neutralized with sodium hydrogencarbonate and extracted three times with EA. The combined organic phases were dried over magnesium sulfate and, after filtering off the desiccant, dried under reduced pressure. 420 mg of the title compound were isolated. LC-MS Rt: 1.64 min [M+H]$^+$:354.0 f) 2-(2,3-Diethoxy-7-iminoimidazo[1,5-b]pyridazin-6-yl)-1-[3-methylamino-5-(pentafluorosulfanyl)phenyl]ethanone as trifluoroacetic acid salt 2,3-Diethoxyimidazo[1,5-b]pyridazin-7-ylamine trifluoroacetic acid salt [example 1k), 10 mg] and 2-bromo-1-[3-methylamino-5-(pentafluorosulfanyl)phenyl]ethanone (18 mg) were reacted with one another, worked up and purified analogously to example 11). For further purification, preparative HPLC was followed by chromatography once more using silica gel (2 g cartridge; DCM/methanol gradient). Combination of the clean fractions was followed by drying. The residue was taken up with ACN/water (+0.05% TFA) and freeze-dried. 4 mg of the title compound were obtained. LC-MS Rt: 1.29 min [M+H]$^+$:491.1

Pharmacological Examples

PAR1 Determination Method: Inhibition of PAR1-Mediated Platelet Aggregation

The pharmacological testing of the substances took place in platelet aggregation induced by TRAP (thrombin receptor-activating peptide) in 96-well format. For this purpose, blood was taken from healthy volunteer donors in 20 ml syringes containing 2 ml of 3.13% sodium citrate solution. After centrifugation at 150×g for 20 minutes, the platelet-rich plasma (PRP) was separated off and mixed with 1 µl of PGE1 solution (500 µg/ml in ethanol)/ml of PRP. Incubation at room temperature for 5 minutes was followed by centrifugation at 120×g for 15 minutes to remove the leukocytes. The leukocyte-free PRP was transferred in 5 ml portions into 15 ml PP tubes and centrifuged at 360×g for 15 minutes in order to pellet the platelets. The plasma was then decanted off and the platelet sediment from 5 ml of PRP was resuspended in 1 ml of Tyrode's (120 mM NaCl, 2.6 mM KCl, 12 mM NaHCO$_3$, 0.39 mM NaH$_2$PO$_4$×H$_2$O, 10 mM HEPES, 0.35% BSA, 5.5 mM glucose, pH 7.4) and adjusted with Tyrode's to a platelet count of 3×10$^5$/microliter (4). 13 ml of this cell suspension were then mixed with 866 µL of 10 mM CaCl$_2$ solution, and 120 µL thereof were pipetted into each well of a 96-well plate containing 15 µL of the substance to be tested. After incubation at room temperature in the dark for 30 minutes, 15 µL of a TRAP solution (70-100 µM) were added as agonist, and kinetics were recorded at 650 nm in a SpectraMax 340 at 37° C. for 20 minutes while shaking. The areas under the curves of negative control (Tyrode's/DMSO) and positive control (15 µl of agonist/DMSO) were calculated and the difference was fixed as the 100% value. The substances to be tested were pipetted as serial dilutions in duplicate determination, the AUC was likewise determined for each substance concentration, and the % inhibition of the AUC compared with the control was calculated. On the basis of the % inhibition, the IC$_{50}$ was calculated by nonlinear regression analysis according to the 4-parameter equation.

Table 1 shows the results.

TABLE 1

| Compound from example | Inhibition of platelet aggregation IC$_{50}$ [micro M] | Compound from example | Inhibition of platelet aggregation IC$_{50}$ [micro M] |
|---|---|---|---|
| 1 | 0.005 | 3 | 0.004 |
| 4 | 0.18 | | |

What is claimed is:
1. A compound of formula I

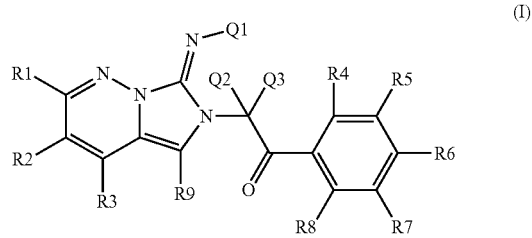

or a stereoisomeric or tautomeric form thereof, or a physiologically compatible salt thereof, where Q1 is a hydrogen atom, —(C$_1$-C$_6$)-alkyl, —(C$_3$-C$_6$)-cycloalkyl, —OH, —O—(C$_1$-C$_6$)-alkyl or —O—(C$_3$-C$_6$)-cycloalkyl, where alkyl and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in alkyl or cycloalkyl may be replaced by fluorine, Q2 and Q3 are the same or different and are each independently a hydrogen atom, —(C$_1$-C$_6$)-alkyl or —(C$_3$-C$_6$)- cycloalkyl, where some or all of the hydrogen atoms in alkyl or cycloalkyl may be replaced by fluorine, R1, R2 and R3 are the same or different and are each independently a hydrogen atom, $-(C_1-C_6)$-alkyl, $-(C_3-C_6)$-cycloalkyl, $-O-(C_1-C_8)$-alkyl, $-O-(C_3-C_6)$-cycloalkyl, $-(C_0-C_4)$-alkylene-C(O)—N(R11)-R12, $-(C_0-C_4)$-alkylene-C(O)—O—R11, $-(C_0-C_4)$-alkylene-C(O)—R11, $-(C_0-C_4)$-alkylene-N(R11)-C(O)—R12, halogen, OH, —CN, —NO$_2$, —SO$_2$CH$_3$, —SO$_2$CF$_3$, —SF$_5$, —Si[—(C$_1$-C$_4$)-alkyl]$_3$, $-(C_1-C_6)$-alkylene-O—(C$_1$-C$_6$)-alkyl, —O—(C$_1$-C$_6$)-alkylene-O—(C$_1$-C$_6$)-alkyl, —O—(C$_0$-C$_4$)-alkylene-(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl; or —O—(C$_1$-C$_4$)-alkylene-(C$_3$-C$_6$)-cycloalkyl; or —(C$_4$-C$_{15}$)-Het, where Het is unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, or —O—(C$_1$-C$_6$)-alkylene-O-(C$_1$-C$_6$)-alkylene-O—(C$_1$-C$_6$)-alkyl, where alkyl, alkylene and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl, —(C$_6$-C$_{14}$)-aryl, where aryl is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; —(C$_4$-C$_{15}$)-Het, where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —O—(C$_3$-C$_6$)-cycloalkyl, or where some or all of the hydrogen atoms in alkyl, alkylene or cycloalkyl may be replaced by fluorine, or R1 and R2, or R2 and R3, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in the 5- to 8-membered ring formed, and in alkyl or cycloalkyl, may be replaced by fluorine, R11 and R12 are each independently a hydrogen atom, —(C$_1$-C$_6$)-alkyl, —(C$_3$-C$_6$)-cycloalkyl, —(C$_0$-C$_4$)-alkylene-(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl; or —(C$_0$-C$_4$)-alkylene-(C$_4$-C$_{15}$)-Het, where Het is unsubstituted or mono-, di-, tri-, tetra- or pentasubstituted independently by halogen, (C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —SO$_2$CH$_3$ or —SO$_2$CF$_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—C(O)" group to form cyclic amines, imides or lactams which contain up to two further heteroatoms from the group of N, O, and S, where the ring is unsubstituted or mono- or disubstituted independently —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in the 5- to 8-membered ring formed, and in alkyl or cycloalkyl, may be replaced by fluorine, R4, R5, R6, R7 and R8 are the same or different and are each independently a hydrogen atom, —(C$_1$-C$_6$)-alkyl, —(C$_3$-C$_6$)-cycloalkyl, OH, —CN, —NO$_2$, —O—(C$_1$-C$_8$)-alkyl, —O—(C$_3$-C$_6$)-cycloalkyl, —(C$_0$-C$_4$)-alkylene-(CO)—N(R21)-R22, —SO$_2$CH$_3$, —SO$_2$CF$_3$, —(C$_0$-C$_4$)-alkylene-C(O)—O—R21, halogen, —SF$_5$, —(C$_0$-C$_4$)-alkylene-C(O)—R21, —(C$_0$-C$_4$)-alkylene-N(R21)-R22, —(C$_0$-C$_4$)-alkylene-N(R21)-C(O)—R22, —(C$_1$-C$_6$)-alkylene-O—(C$_1$-C$_6$)-alkyl, —(C$_0$-C$_6$)-alkylene-O—(C$_1$-C$_6$)-alkylene-O—(C$_1$-C$_6$)-alkyl, —Si[—(C$_1$-C$_4$)-alkyl]$_3$, —(C$_0$-C$_6$)-alkylene-O—(C$_1$-C$_4$)-alkylene-(C$_3$-C$_6$)-cycloalkyl, —(C$_0$-C$_6$)-alkylene-O—(C$_0$-C$_6$)-alkylene-(C$_6$-C$_{14}$)-aryl or —(C$_4$-C$_{15}$)-Het, where alkyl, alkylene and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl, —(C$_6$-C$_{14}$)-aryl, where aryl is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —(C$_4$-C$_{15}$)-Het, where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —O—(C$_3$-C$_6$)-cycloalkyl, where some or all of the hydrogen atoms in alkyl, alkylene or cycloalkyl may be replaced by fluorine, or R4 and R5, R5 and R6, R6 and R7, or R7 and R8, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in the 5- to 8-membered ring formed, and in alkyl or cycloalkyl, may be replaced by fluorine, R9 is a hydrogen atom, —(C$_1$-C$_6$)-alkyl, —(C$_3$-C$_6$)-cycloalkyl, —(C$_0$-C$_4$)-alkylene-(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl; or —(C$_0$-C$_4$)-alkylene-(C$_4$-C$_{15}$)-Het, where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, and where all or some of the hydrogen atoms in alkyl, alkylene or cycloalkyl may be replaced by fluorine, R21 and R22 are each independently a hydrogen atom, —(C$_1$-C$_6$)-alkyl, —(C$_3$-C$_6$)-cycloalkyl, —(C$_0$-C$_4$)-alkylene-(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl; or —(C$_0$-C$_4$)-alkylene-(C$_4$-C$_{15}$)-Het, where Het is unsubstituted or mono-, di-, tri-, tetra- or pentasubstituted independently by halogen, (C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —SO$_2$CH$_3$ or —SO$_2$CF$_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to two further heteroatoms from the group of N, O and S, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in the 5- to 8-membered ring formed, and in alkyl or cycloalkyl, may be replaced by fluorine.

2. A compound as claimed in claim 1, wherein

Q1, Q2 and Q3 are the same or different and are each independently a hydrogen atom, —(C$_1$-C$_6$)-alkyl or —(C$_3$-C$_6$)-cycloalkyl, where some or all of the hydrogen atoms in alkyl or cycloalkyl may be replaced by fluorine, R1, R2 and R3 are the same or different and are each independently a hydrogen atom, —(C$_1$-C$_6$)-alkyl, —(C$_3$-C$_6$)-cycloalkyl, —O—(C$_1$-C$_8$)-alkyl, —O—(C$_3$-C$_6$)-cycloalkyl, —(C$_0$-C$_4$)-alkylene-C(O)—N(R11)-R12, —(C$_0$-C$_4$)-alkylene-C(O)—O—R11, —(C$_0$-C$_4$)-alkylene-C(O)—R11, —(C$_0$-C$_4$)-alkylene-N(R11)-R12, —(C$_0$-C$_4$)-alkylene-N(R11)-C(O)—R12, halogen, OH, —CN, —NO$_2$, —SO$_2$CH$_3$, —SO$_2$CF$_3$, —SF$_5$, —Si[—(C$_1$-C$_4$)-alkyl]$_3$, —(C$_1$-C$_6$)-alkylene-O—(C$_1$-C$_6$)-alkyl, —O—(C$_1$-C$_6$)-alkylene-O—(C$_1$-C$_6$)-alkyl, —O—(C$_0$-C$_4$)-alkylene-(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl; or —O—(C$_1$-C$_4$)-alkylene-(C$_3$-C$_6$)-cycloalkyl; or —(C$_4$-C$_{15}$)-Het, where Het is unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —O—(C$_1$-C$_6$)-alkylene-O—(C$_1$-C$_6$)-alkylene-O—(C$_1$-C$_6$)-alkyl, where alkyl, alkylene and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl, —(C$_6$-C$_{14}$)-aryl, where aryl is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; (C$_4$-C$_{15}$)-Het, where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —O—(C$_3$-C$_6$)-cycloalkyl, or where some or all of the hydrogen atoms in alkyl, alkylene or cycloalkyl may be replaced by fluorine, with the proviso that at least one R1, R2 or R3 is not a hydrogen atom, or R1 and R2 or R2 and R3, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in alkyl or cycloalkyl may be replaced by fluorine, R11 and R12 are each independently a hydrogen atom, —(C$_1$-C$_6$)-alkyl, —(C$_3$-C$_6$)-cycloalkyl, —(C$_0$-C$_4$)-alkylene-(C$_6$-C$_{14}$)-aryl, where aryl is unsubstituted or mono-, di- or trisubstituted independently by —O—(C$_1$-C$_6$)-alkyl, —(C$_1$-C$_4$)-alkyl, OH, —(C$_3$-C$_6$)-cycloalkyl or —O—(C$_3$-C$_6$)-cycloalkyl; or —(C$_0$-C$_4$)-alkylene-(C$_4$-C$_{15}$)-Het, where Het is unsubstituted or mono-, di-, tri-, tetra- or pentasubstituted independently by halogen, (C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl or —SO$_2$CH$_3$ or —SO$_2$CF$_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring which is formed together with the nitrogen atom "N" or the "N—(CO)" group to form cyclic amines, imides or lactams which contain up to two further heteroatoms from the group of N, O and S, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in alkyl or cycloalkyl may be replaced by fluorine, R4, R5, R6, R7 and R8 are the same or different and are each independently a hydrogen atom, —(C$_1$-C$_6$)-alkyl, —(C$_3$-C$_6$)-cycloalkyl, OH, —CN, —NO$_2$, —O—(C$_1$-C$_8$)-alkyl, —O—(C$_3$-C$_6$)-cycloalkyl, —(C$_0$-C$_4$)-alkylene-(CO)—N(R21)-R22, —SO$_2$CH$_3$, —SO$_2$CF$_3$, —(C$_0$-C$_4$)-alkylene-C(O)—O—R21, halogen, —SF$_5$, —(C$_0$-C$_4$)-alkylene-C(O)—R21, —(C$_0$-C$_4$)-alkylene-N(R21)-R22, —(C$_0$-C$_4$)-alkylene-N(R21)-C(O)—R22, —(C$_1$-C$_6$)-alkylene-O—(C$_1$-C$_6$)-alkyl, —(C$_0$-C$_6$)-alkylene-β-(C$_1$-C$_6$)-alkylene-O—(C$_1$-C$_6$)-alkyl, —Si[—(C$_1$-C$_4$)-alkyl]$_3$, —(C$_0$-C$_6$)-alkylene-O—(C$_1$-C$_4$)-alkylene-(C$_3$-C$_6$)-cycloalkyl, —(C$_0$-C$_6$)-alkylene-O—(C$_0$-C$_6$)-alkylene-(C$_6$-C$_{14}$)-aryl or —(C$_4$-C$_{15}$)-Het, where alkyl, alkylene and cycloalkyl are each unsubstituted or mono-, di- or trisubstituted independently by —(C$_1$-C$_4$)-alkyl, —(C$_3$-C$_6$)-cycloalkyl, OH, —O—(C$_1$-C$_6$)-alkyl, —(C$_6$-C$_{14}$)-aryl, where aryl is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —(C$_4$-C$_{15}$)-Het, where Het is unsubstituted or mono-, di-, tri-, tetra- or pentasubstituted independently by halogen, —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl; or —O—(C$_3$-C$_6$)-cycloalkyl, or where some or all of the hydrogen atoms in alkyl, alkylene or cycloalkyl may be replaced by fluorine, with the proviso that at least one R4, R5, R6, R7 or R8 is not a hydrogen atom, or R4 and R5, R5 and R6, R6 and R7 or R7 and R8, together with the ring atoms to which they are each bonded, form a 5- to 8-membered ring, where the ring consists only of carbon atoms or 1, 2 or 3 of these atoms are replaced by nitrogen, oxygen or sulfur atoms, where the ring is unsubstituted or mono- or disubstituted independently by —(C$_1$-C$_4$)-alkyl, —(C$_3$-C$_6$)-cycloalkyl, OH, —O—(C$_1$-C$_6$)-alkyl or —O—(C$_3$-C$_6$)-cycloalkyl, where some or all of the hydrogen atoms in alkyl or cycloalkyl may be replaced by fluorine, R9 is a hydrogen atom, —(C$_1$-C$_6$)-alkyl, —(C$_3$-C$_6$)-cycloalkyl, —(C$_0$-C$_4$)-alkylene-(C$_6$-C$_4$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl; or —($C_0$-$C_4$)-alkylene-($C_4$-$C_{15}$)-Het, where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl, and where all or some of the hydrogen atoms in alkyl, alkylene or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, where aryl is unsubstituted or mono-, di- or trisubstituted independently by —O—($C_1$-$C_6$)-alkyl, —($C_1$-$C_4$)-alkyl, OH, —($C_3$-$C_6$)-cycloalkyl or —O—($C_3$-$C_6$)-cycloalkyl; or —($C_0$-$C_4$)-alkylene-($C_4$-$C_{15}$)-Het, where Het is unsubstituted or mono-, di-, tri-, tetra- or pentasubstituted independently by halogen, ($C_1$-$C_4$)-alkyl, —($C_3$-$C_6$)-cycloalkyl, OH, —O—($C_1$-$C_6$)-alkyl or —O—($C_3$-$C_6$)-cycloalkyl; —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring which is formed together with the nitrogen atom "N" or the "N—C(O)" group to form cyclic amines, imides or lactams which contain up to two further heteroatoms from the group of N, O and S, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

3. A compound as claimed in claim 1, wherein

Q1, Q2 and Q3 are the same or different and are each independently a hydrogen atom, —($C_1$-$C_6$)-alkyl or —($C_3$-$C_6$)-cycloalkyl, where some or all of the hydrogen atoms in alkyl or cycloalkyl may be replaced by fluorine, R1, R2 and R3 are the same or different and are each independently a hydrogen atom, —($C_1$-$C_6$)-alkyl, —($C_3$-$C_6$)-cycloalkyl, —O—($C_1$-$C_8$)-alkyl, —O—($C_3$-$C_6$)-cycloalkyl, —($C_0$-$C_4$)-alkylene-C(O)—N(R11)-R12, —($C_0$-$C_4$)-alkylene-C(O)—O—R11, —($C_0$-$C_4$)-alkylene-C(O)—R11, —($C_0$-$C_4$)-alkylene-N(R11)-R12, —($C_0$-$C_4$)-alkylene-N(R11)-C(O)—R12, halogen, OH, —CN, —$NO_2$, —$SO_2CH_3$, —Si[—($C_1$-$C_4$)-alkyl]$_3$, —($C_1$-$C_6$)-alkylene-O—($C_1$-$C_6$)-alkyl, —O—($C_1$-$C_6$)-alkylene-O—($C_1$-$C_6$)-alkyl, —O—($C_0$-$C_4$)-alkylene-($C_6$-$C_{14}$)-aryl, —O—($C_1$-$C_4$)-alkylene-($C_3$-$C_6$)-cycloakl, —($C_4$-$C_{15}$)-Het or —O—($C_1$-$C_6$)-alkylene-O—($C_1$-$C_6$)-alkylene-O—($C_1$-$C_6$)-alkyl, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, or where some or all of the hydrogen atoms in alkyl, alkylene or cycloalkyl may be replaced by fluorine, with the proviso that at least one R1, R2 or R3 is not a hydrogen atom, or R1 and R2, or R2 and R3, together with the ring atoms to which they are each bonded, form a ring selected from the group of 2,3,5,6,7,8-hexahydro-1,2,3a,4,5,8-hexaaza-cyclopenta[b]naphthalene; 2,6,7,8-tetrahydro-3H-5-oxa-1,2,3a,4,8-pentaaza-cyclopenta[b]naphthalene; 2,3,6,7-tetrahydro-5,8-dioxa-1,2,3a,4-tetraaza-cyclopenta[b]naphthalene; 2,3,6,7-tetrahydro-5H-8-oxa-1,2,3a,4,5-pentaaza-cyclopenta[b]naphthalene; 2,6,7,8-tetrahydro-3H-5-thia-1,2,3a,4,8-pentaaza-cyclopenta[b]naphthalene; 2,3,6,7,8,9-hexahydro-1,2,3a,4,6,9-hexaazacyclopenta[a]naphthalene; 2,3-dihydro-5,7-dioxa-1,2,3a,4-tetraaza-s-indacene; 2,6,7,8-tetrahydro-3H-cyclopenta[e][1,2,4]triazolo[4,3-b]pyridazine; 2,7,8,9-tetrahydro-3H-cyclopenta[d][1,2,4]triazolo[4,3-b]pyridazine and 2,3,6a,9a-tetrahydro-[1,3]dioxolo[4,5-d][1,2,4]triazolo[4,3-b]pyridazine, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, R11 and R12 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R11 and R12 in the "N(R11)-R12" and "N(R11)-C(O)—R12" fragments represent a 5- to 8-membered ring, selected from the group of azetidinyl, pyrrolidinyl, piperidinyl, piperazinyl, azepinyl, morpholinyl, thiomorpholinyl, pyrrolidine-2.5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, R4, R5, R6, R7 and R8 are the same or different and are each independently a hydrogen atom, —($C_1$-$C_6$)-alkyl, —($C_3$-$C_6$)-cycloalkyl, OH, —CN, —$NO_2$, —O—($C_1$-$C_8$)-alkyl, —O—($C_3$-$C_6$)-cycloalkyl, —($C_0$-$C_4$)-alkylene-(CO)—N(R21)-R22, —$SO_2CH_3$, —$SO_2CF_3$, —($C_0$-$C_4$)-alkylene-C(O)—O—R21, halogen, —$SF_5$, —($C_0$-$C_4$)-alkylene-C(O)—R21, —($C_0$-$C_4$)-alkylene-N(R21)-R22, —($C_0$-$C_4$)-alkylene-N(R21)-C(O)—R22, —($C_1$-$C_6$)-alkylene-O—($C_1$-$C_6$)-alkyl, —($C_0$-$C_6$)-alkylene-O—($C_1$-$C_6$)-alkylene-O—($C_1$-$C_6$)-alkyl, —Si[—($C_1$-$C_4$)-alkyl]$_3$, —($C_0$-$C_6$)-alkylene-O—($C_1$-$C_4$)-alkylene-($C_3$-$C_6$)-cycloalkyl, —($C_0$-$C_6$)-alkylene-O—($C_0$-$C_6$)-alkylene-($C_6$-$C_{14}$)-aryl or —($C_4$-$C_{15}$)-Het, where alkyl, alkylene and cycloalkyl are each unsubstituted or mono-, di- or trisubstituted independently by —($C_1$-$C_4$)-alkyl, —($C_3$-$C_6$)-cycloalkyl, OH, —O—($C_1$-$C_6$)-alkyl, —($C_6$-$C_{14}$)-aryl, where aryl is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl; —($C_4$-$C_{15}$)-Het, where Het is unsubstituted or mono-, di-, tri-, tetra- or pentasubstituted independently by halogen, —($C_1$-$C_4$)-alkyl, —($C_3$-$C_6$)-cycloalkyl, OH, —O—($C_1$-$C_6$)-alkyl or —O—($C_3$-$C_6$)-cycloalkyl; or —O—($C_3$-$C_6$)-cycloalkyl, or where some or all of the hydrogen atoms in alkyl, alkylene or cycloalkyl may be replaced by fluorine, with the proviso that at least one R4, R5, R6, R7 or R8 is not a hydrogen atom, or R5 and R6, R6 and R7, or R7 and R8, together with the ring atoms to which they are each bonded, form a 5- to 8-membered ring selected from the group of 2,3-dihydrobenzo[1,4]dioxin; 3,4-dihydro-2H-benzo[1,4]oxazine; 1,2,3,4-tetrahydroquinoxaline; benzo[1,3]dioxole; 3,4-dihydro-2H-benzo[1,4]thiazine and 2,3,4,5- tetrahydro-1H-benzo[b][1,4]diazepine, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine, R9 is a hydrogen atom, —($C_1$-$C_6$)-alkyl or —($C_3$-$C_6$)-cycloalkyl, where some or all of the hydrogen atoms in alkyl or cycloalkyl may be replaced by fluorine, R21 and R22 are each independently a hydrogen atom, —($C_1$-$C_6$)-alkyl, —($C_3$-$C_6$)-cycloalkyl, —($C_0$-$C_4$)-alkylene-($C_6$-$C_{14}$)-aryl, —($C_0$-$C_4$)-alkylene-($C_4$-$C_{15}$)-Het, —$SO_2CH_3$ or —$SO_2CF_3$, where some or all of the hydrogen atoms in alkyl, alkylene or cycloalkyl may be replaced by fluorine, or R21 and R22 in the "N(R21)-R22" and "N(R21)-C(O)—R22" fragments represent a 5- to 8-membered ring selected from the group of azetidinyl, pyrrolidinyl, piperidinyl, piperazinyl, azepinyl, morpholinyl, thiomorpholinyl, pyrrolidine-2.5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl, where the ring is unsubstituted or mono- or disubstituted independently by —($C_1$-$C_4$)-alkyl, —($C_3$-$C_6$)-cycloalkyl, OH, —O—($C_1$-$C_6$)-alkyl or —O—($C_3$-$C_6$)-cycloalkyl, where some or all of the hydrogen atoms in alkyl or cycloalkyl may be replaced by fluorine.

4. A compound as claimed in claim 1, wherein
Q1, Q2 and Q3 are the same and are each independently a hydrogen atom,
R1, R2 and R3 are the same or different and are each independently a hydrogen atom, —($C_1$-$C_4$)-alkyl, —O—$CH_2$—$CF_3$ or —O—($C_1$-$C_6$)-alkyl, with the proviso that at least one R1, R2 or R3 is not a hydrogen atom,
R4, R5, R6, R7 and R8 are the same or different and are each independently a hydrogen atom, —($C_1$-$C_6$)-alkyl, —O—($C_1$-$C_4$)-alkyl, —$SF_5$ or —N(R21)-R22, with the proviso that at least one R4, R5, R6, R7 or R8 is not a hydrogen atom,
R9 is a hydrogen atom,
R21 and R22 are each independently a hydrogen atom or —($C_1$-$C_4$)-alkyl, or
R21 and R22 in the "N(R21)-R22" fragment are each a 5- to 8-membered ring selected from the group of azetidinyl, pyrrolidinyl, piperidinyl, piparazinyl, azepinyl, imidazolyl, morpholinyl, thiomorpholinyl, pyrrolidine-2,5-dionyl, piperidine-2,6-dionyl, piperazine-2,6-dionyl, morpholine-3,5-dionyl, pyrrolidin-2-onyl, piperidin-2-onyl, piperazin-2-onyl and morpholin-3-onyl.

5. A compound as claimed in claim 1, wherein the compound is selected from:
1-(3-tert-butyl-4-methoxy-5-morpholin-4-ylphenyl)-2-(7-imino-2,3-dimethoxyimidazo[1,5-b]pyridazin-6-yl)ethanone,
1-(3-tert-butyl-4-methoxy-5-morpholin-4-ylphenyl)-2-(2,3-diethoxy-7-iminoimidazo[1,5-b]-pyridazin-6-yl)ethanone,
N-{3-[2-(2,3-diethoxy-7-iminoimidazo[1,5-b]pyridazin-6-yl)acetyl]-5-pentafluorosulfanylphenyl}acetamide,
1-(3-tert-butyl-4-methoxy-5-morpholin-4-ylphenyl)-2-[7-imino-2-methoxy-3-(2,2,2-trifluoroethoxy)imidazo[1,5-b]pyridazin-6-yl]ethanone,
2-(2,3-diethoxy-7-iminoimidazo[1,5-b]pyridazin-6-yl)-1-(5-methylamino-3-pentafluorosulfanyl-phenyl)ethanone or
2-(2,3-diethoxy-7-iminoimidazo[1,5-b]pyridazin-6-yl)-1-[3-methylamino-5-(pentafluoro-sulfanyl)phenyl]ethanone.

6. A pharmaceutical composition comprising at least one compound as claimed in claim 1 and a pharmaceutically acceptable carrier.

7. A method for the treatment of a disorder associated with thromboses, embolisms, or hypercoagulability, the method comprising administering to a patient in need thereof an effective dose of a compound as claimed in claim 1.

8. The method as claimed in claim 7, wherein the disorder is myocardial infarction, angina pectoris, acute coronary syndrome, stroke, peripheral vascular disorders, deep vein thrombosis, pulmonary embolism, embolic or thrombotic events caused by cardiac arrhythmias, restenosis following revascularization and angioplasty, reduction of the risk of thrombosis following surgical procedures, procedures leading to contact of blood with foreign surfaces, and atherosclerosis.

9. A process for preparing a compound of formula I as claimed in claim 1, comprising
a) reacting a compound of formula II

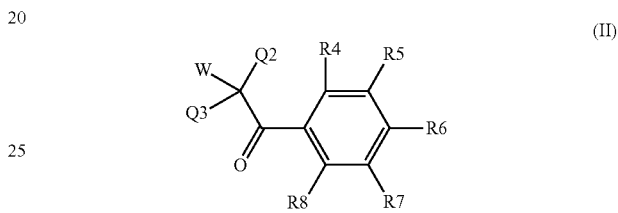

where R4, R5, R6, R7, R8, Q2 and Q3 are each as defined in claim 1 and W is chloride, bromide, mesylate or tosylate with a compound of formula III

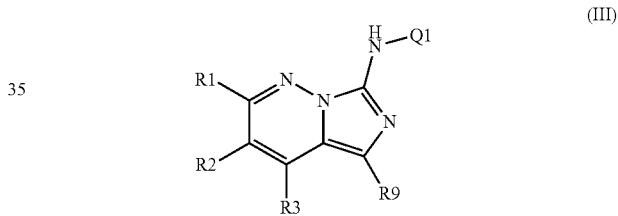

where R1, R2, R3, R9 and Q1 are each as defined in claim 1, with or without addition of base, in a solvent to give a compound of formula I, or
b) reacting a compound of formula VII with a compound of formula VIII,

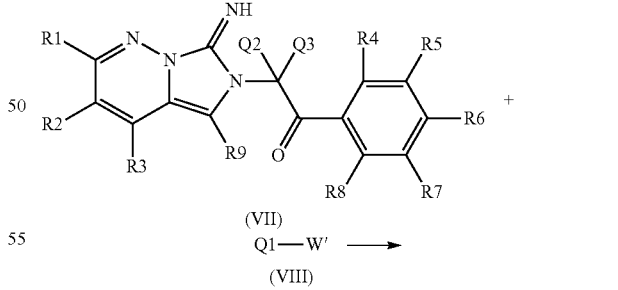

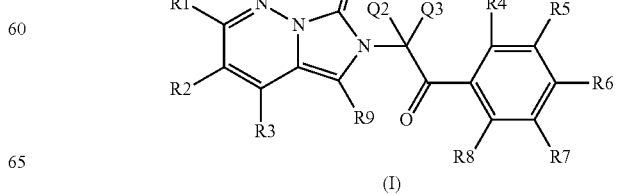

where R1, R2, R3, R4, R5, R6, R7, R8, R9, Q1, Q2 and Q3 are each as defined in claim 1 with a compound Q1-W' where W' is a leaving group, with or without addition of base, to give a compound of formula I, or c) reacting a compound of formula XXVI

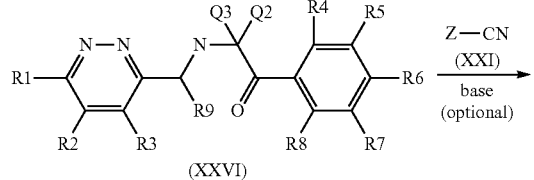

(XXVI)

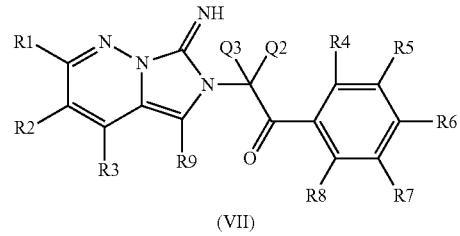

(VII)

where R1, R2, R3, R4, R5, R6, R7, R8, R9, Q1, Q2 and Q3 are each as defined in claim 1 with a compound Z—CN, where Z is a leaving group, with or without addition of base, to give a compound of the formula VII, or d) reacting a compound of formula XXVII

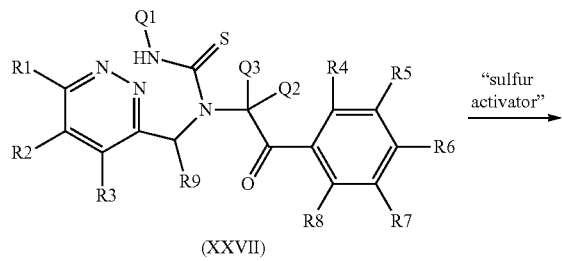

(XXVII)

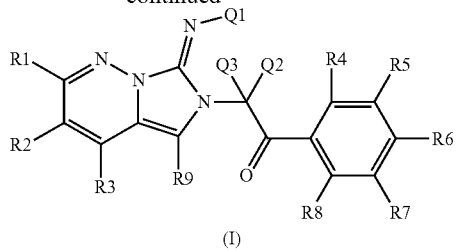

(I)

where R1, R2, R3, R4, R5, R5, R7, R8, R9, Q1, Q2 and Q3 are each as defined in claim 1 with a sulfur activator to give a compound of formula I, or e) either isolating the compound of formula I prepared by methods a) to d) in free form or releasing it from physiologically incompatible salts or, in the case of the presence of acidic or basic groups, converting it to physiologically compatible salts, or f) separating a compound of formula I prepared by methods a) to d), or a suitable precursor of the formula I which, owing to its chemical structure, occurs in enantiomeric or diastereomeric forms, into the pure enantiomers or diastereomers by salt formation with enantiomerically pure acids or bases, chromatography on chiral stationary phases or derivatization by means of chiral enantiomerically pure compounds, separation of the diastereomers thus obtained, and elimination of the chiral auxiliary groups.

10. The process of claim 9, wherein, for step (b), W' is selected from chloride, bromide, tosylate, mesylate, and methylsulfate; for step (c), Z is selected from tosylate, chloride, and bromide; and for step (f), the enantiomerically pure compounds are amino acids.

* * * * *